(12) United States Patent
Li

(10) Patent No.: US 8,125,641 B2
(45) Date of Patent: Feb. 28, 2012

(54) METHOD AND APPARATUS FOR PHASE-COMPENSATED SENSITIVITY-ENHANCED SPECTROSCOPY (PCSES)

(75) Inventor: Guoguang Li, Fremont, CA (US)

(73) Assignee: n&k Technology, Inc., San Jose, CA (US)

( * ) Notice: Subject to any disclaimer, the term of this patent is extended or adjusted under 35 U.S.C. 154(b) by 526 days.

(21) Appl. No.: 12/383,864

(22) Filed: Mar. 27, 2009

(65) Prior Publication Data

US 2010/0245819 A1    Sep. 30, 2010

(51) Int. Cl.
*G01J 4/00* (2006.01)
(52) U.S. Cl. ....................................... 356/369
(58) Field of Classification Search .......... None
See application file for complete search history.

(56) References Cited

U.S. PATENT DOCUMENTS 4,053,232 A    10/1977    Dill
(Continued)

FOREIGN PATENT DOCUMENTS
JP        05-264227      10/1993
(Continued)

OTHER PUBLICATIONS

Fanton, "A novel technique for performing ellipsometric measurements in a sub-micrometer area", SPIE vol. 2004 Interferometry VI: Applications, 1993, pp. 313.

(Continued)

*Primary Examiner* — Gregory J Toatley
*Assistant Examiner* — Juan D Valentin
(74) *Attorney, Agent, or Firm* — Lumen Patent Firm

(57) ABSTRACT

A method and apparatus for convolving spectroscopic data with certain phase information for practicing phase-compensated sensitivity-enhanced spectroscopy (PCSES). PCSES uses a beam of radiation in a polarization state $PS_p$ from a source emitting at a plurality of wavelengths, and places in the beam a compensator capable of altering polarization state $PS_p$ by applying a delimited phase shift $\Delta$ between two orthogonal polarization axes of the radiation to restrict a finely-vibrating spectrum. A sample disposed in the beam after the compensator generates a response beam by reflection, transmission or even both. A polarization state $PS_a$ of the response beam is passed to a detector to determine a spectrum of the response beam. A first spectrum is collected when polarization states $PS_p$, $PS_a$ and the compensator are in a first polarization-altering configuration and a second spectrum is collected when polarization states $PS_p$, $PS_a$ and the compensator are in a second polarization-altering configuration. A phase-compensated spectrum is then derived from just the first and second spectra thereby allowing the user to undertake optical characterization, including the measurement of film thickness t and complex indices of refraction n, k of the sample with as few as just two polarization-altering configurations.

33 Claims, 11 Drawing Sheets

U.S. PATENT DOCUMENTS

| | | | |
|---|---|---|---|
| 4,668,086 A | 5/1987 | Redner |
| 4,905,170 A | 2/1990 | Forouhi |
| 4,999,014 A | 3/1991 | Gold |
| 5,181,080 A | 1/1993 | Fanton |
| 5,329,357 A | 7/1994 | Bernoux |
| 5,373,359 A | 12/1994 | Woollam |
| 5,504,582 A | 4/1996 | Johs |
| 5,521,706 A | 5/1996 | Green |
| 5,596,406 A | 1/1997 | Rosencwaig |
| 5,716,212 A | 2/1998 | Lee |
| 5,757,494 A | 5/1998 | Green |
| 5,872,630 A | 2/1999 | Johs |
| 5,877,859 A | 3/1999 | Aspnes |
| 5,880,831 A | 3/1999 | Buermann |
| 5,929,995 A | 7/1999 | Johs |
| 5,963,329 A | 10/1999 | Conrad |
| 5,973,787 A | 10/1999 | Aspnes |
| 5,991,022 A | 11/1999 | Buermann |
| 6,034,777 A | 3/2000 | Johs |
| 6,134,012 A | 10/2000 | Aspnes |
| 6,222,199 B1 | 4/2001 | Freeouf |
| 6,320,657 B1 | 11/2001 | Aspnes |
| 6,392,756 B1 | 5/2002 | Li |
| 6,429,943 B1 | 8/2002 | Opsal |
| 6,449,043 B2 | 9/2002 | Aspnes |
| 6,483,580 B1 | 11/2002 | Xu |
| 6,583,875 B1 | 6/2003 | Wei |
| 6,650,415 B2 | 11/2003 | Aspnes |
| 6,831,743 B2 | 12/2004 | Aspnes |
| 6,982,791 B2 | 1/2006 | Opsal |
| 7,075,649 B1 | 7/2006 | Johs |
| 7,193,710 B1 | 3/2007 | Johs |
| 7,286,243 B2 | 10/2007 | Rosencwaig |
| 7,304,737 B1 | 12/2007 | Liphardt |
| 7,355,708 B2 | 4/2008 | Aspnes |
| 7,489,399 B1 | 2/2009 | Lee |
| 7,492,455 B1 | 2/2009 | Johs |
| 2006/0268272 A1 | 11/2006 | Liphardt |
| 2007/0146706 A1* | 6/2007 | Garcia-Caurel et al. ...... 356/369 |
| 2007/0229826 A1* | 10/2007 | Schubert ...................... 356/369 |

FOREIGN PATENT DOCUMENTS

| | | |
|---|---|---|
| JP | 07-091925 | 4/1995 |
| JP | 2004-138519 | 5/2004 |
| WO | WO 01/90687 | 11/2001 |

OTHER PUBLICATIONS

Opsal, "Broadband spectral operation of a rotating-compensator ellipsometer", Thin Solid Films, vol. 313-314, Feb. 13, 1998, pp. 58-61.

Lee, "Dual rotating-compensator multichannel ellipsometer: Instrument development for high-speed Mueller matrix spectroscopy of surfaces and thin films", Review of Scientific Instruments, vol. 72, 1742 (Mar. 2001).

Silver, "Fundamental Limits of Optical Critical Dimension Metrology: A Simulation Study", Proc. Of SPIE, vol. 6518 65180U-1, 2007.

Otani, "Spectroscopic Mueller matrix polarimeter using four channeled spectra", Frontiers in Optics, Optical Society of America Technical Digest, 2008.

Okabe, "Spectroscopic polarimetry using channeled spectroscopic polarization state generator (CSPSG)", Optics Express, vol. 15, No. 6, Mar. 19, 2007 pp. 3039.

Oka, "Static Spectroscopic Ellipsometer Based on Optical Frequency-Domain Interferometry," *Polarization Analysis and Measurement IV*, D. H. Goldstein, D. B. Chenault, W. G. Egan, and M. J. Duggin, eds., Proc. SPIE 4481, 2001, pp. 137-140.

* cited by examiner

METHOD AND APPARATUS FOR PHASE-COMPENSATED SENSITIVITY-ENHANCED SPECTROSCOPY (PCSES)

FIELD OF THE INVENTION

This invention relates generally to optical characterization, and especially to the measurement of optical properties expressed by the complex index of refraction (n, k) and physical parameters such as thickness (t) of samples including thin films.

BACKGROUND ART

Optical characterization or measurement of optical properties of various samples has become an important measurement and quality control technique due to its non-destructive nature. Specifically, optical characterization is commonly used to obtain the complex index of refraction, i.e., the values of n and k, as well as physical parameters of which the most important one is thickness t. Among the many types of samples whose optical properties and physical parameters can be characterized in this manner, the most important ones are samples with thin film layers. More accurate and reliable approaches to characterizing such samples are driven by an acute need in the semiconductor industry, which works with wafers covered by ultra thin oxide film layers.

For over a century now, the two traditional optical characterization techniques used in commerce and by the semiconductor industry include spectrometry and ellipsometry. Ellipsometry was introduced by P. Drude over a century ago in "Über oberflächenschichten," Annalen der Physik 36, 1889, pp. 532-560 and pp. 865-897. Spectrometry was also introduced over a century ago. Both of these techniques are non-destructive and have in-situ capabilities. They are also well-understood and have already manifested much of their great potential to be practiced over wide spectral ranges. Still, each of these techniques also has its unique advantages and disadvantages. These limit how certain aspects of spectroscopy and ellipsometry can be combined and leveraged to improve optical characterization methods and apparatus. To better address these issues, we will first briefly review spectrometry and ellipsometry separately.

Spectrometry and Related Methods

Spectrophotometers, or just spectrometers, are typically easy to make, and they usually cover a very broadband wavelength range. Most commercial metrology tools using spectrometers have high signal-to-noise ratios (SNR) and are, when based on a suitable dispersion model, capable of characterizing semitransparent films (i.e., simultaneously determining n, k and t) down to about 150 Å. An example of a useful dispersion model is the Forouhi-Bloomer method found in U.S. Pat. No. 4,905,170. Further, U.S. Pat. Nos. 5,880,831 and 5,991,022 teach thin film metrology systems employing spectroscopy in the reflectance mode, i.e., reflectometry, with the Forouhi-Bloomer dispersion relations.

Many spectroscopic techniques have been developed to measure thinner films. U.S. Pat. No. 6,392,756 teaches enhancement of signal from a very thin carbon film in the measurement. When this carbon film is deposited on top of a thick ($\approx$3,000 Å) $SiO_2$ film on an opaque substrate, instead of directly on the opaque substrate, then the n, k and t values of the thin film can be simultaneously determined for films as thin as 50 Å. Unfortunately, these special samples are not always available or relevant to the metrology needs at hand.

U.S. Pat. No. 4,999,014 to Gold et al. describes a beam-profile relectometry (BPR) method that relies on focusing a normally incident beam onto the sample at a high numerical aperture (NA) to provide a range of incident angles at the sample. Analysis of the resulting angle-dependent s- and p-polarizations in the reflectance data can be used for film characterization, such as deriving film thickness t. The accuracy of this method usually deteriorates for film thicknesses below 50 Å. We note that with improvements to the analysis of signals at different angles of incidence in the BPR method, e.g., as taught by Opsal et al. in U.S. Pat. No. 6,429,943, this approach can also be used for measuring periodic structures. To overcome the 50 Å thickness limit of BPR, the operating wavelength can be decreased to vacuum ultra-violet (VUV), since shorter wavelengths may yield stronger signals for thin films, as illustrated in U.S. Pat. No. 6,222,199. However, this makes the system more costly and cumbersome, since all measurements need to be done inside a vacuum chamber.

Generally speaking, it has been observed that as film thickness t decreases towards zero the sensitivity of spectrometers to t decreases and the measurements become more tedious and less reliable. Pure spectrometry has thus inherited the corresponding limitation.

Ellipsometry and Related Methods

Ellipsometry is generally defined as the measurement of the state of polarization of a polarized light wave or radiation, and is conducted in order to obtain information about an optical system that modifies the state of polarization. During an ellipsometric experiment, polarized radiation is allowed to interact with the optical system or sample under investigation. This interaction changes the radiation's state of polarization. A common description of the state of polarization employs the ellipsometric angles $\psi$ and $\Delta$. These angles are defined in FIG. 1, where IP is the incidence plane, $\theta_i$ is the angle of incidence, $r_s$ and $r_p$ are the reflection coefficients for s- and p-polariations of the radiation (s- is "senkrecht" or perpendicular and p- is parallel to incidence plane IP). Measurements of the initial and final states of polarization are used to determine the system's transformation properties, as described by its Jones or Mueller matrix.

In 1852 G. G. Stokes introduced a description of the state of polarization with four quantities, or Stokes parameters, which are functions only of observables of the electromagnetic radiation. The state of polarization of a beam of radiation is thus described in terms of these Stokes parameters, $S_0 \ldots S_3$ arranged in a Stokes vector as follows:

$$\bar{S} = \begin{pmatrix} S_o \\ S_1 \\ S_2 \\ S_3 \end{pmatrix} = \begin{pmatrix} I_o \\ I_x - I_y \\ I_{+\frac{\pi}{4}} - I_{-\frac{\pi}{4}} \\ I_r - I_l \end{pmatrix}.$$

The I's stand for intensities and subscripts indicate directions: x and y are the horizontal and vertical directions, $+\pi/4$ and $-\pi/4$ are the $+45°$ and $-45°$ azimuths, and r and l are right and left circular directions.

To use Stokes vectors one needs a formalism to describe the effect of optical components on polarization in terms of Stokes vectors. Mueller introduced a formalism that describes each optical component by a 4×4 matrix. Multiplying this Mueller matrix with a Stokes vector results in a new Stokes vector describing the polarization state of the light beam just behind the component. This procedure is repeated to describe a complete train of optical components by one Mueller matrix, which is a product of component Mueller matrices.

Another formalism to describe the state of polarization and its transformation under the influence of optical components, is presented by Clark Jones. Instead of dealing with directly observable quantities such as intensity I, the Jones formalism uses the electric field vector. This 2-element Jones vector is transformed by an optical component 2×2 Jones matrix into a similar Jones vector. Any optical component represented by a Jones matrix may also be expressed by a Mueller matrix. The opposite is not true: only a pure Mueller matrix can be transformed into a Jones matrix. Optical components represented by pure Mueller matrices are also designated as totally polarizing and nondepolarizing.

With these theoretical underpinnings ellipsometry brings powerful tools to optical sample analysis. In particular, ellipsometers measuring the change in polarization of light upon reflection from a sample turn out to be highly sensitive to small changes in thickness t of thin films on the sample. A common ellipsometric system includes a linear polarizer (P), an optional compensator (C) (or retarder (R)), a sample (S) and a second linear polarizer usually called an analyzer (A). Usually, one of the components is rotating continuously during the measurement, which results in either a rotating polarizer ellipsometer (RPE), a rotating analyzer ellipsometer (RAE), or a rotating compensator ellipsometer (RCE).

Rotating compensator ellipsometry (RCE) offers several distinct advantages compared to other ellipsometry methods. Among these advantages are: non-ambiguous determination of $\Delta$, insensitivity to source and detector polarization, no need for a DC level (since RCE determines 5 Fourier coefficients) and possibility to determine all Stokes parameters. An early example of a rotating compensator ellipsometer employing monochromatic light is taught by Dill in U.S. Pat. No. 4,053,232. For an RPE or RAE arrangement without a compensator, only cos $\Delta$ is typically registered and used to obtain $\Delta$. This function of $\Delta$, however, is insensitive near $\Delta=0°$ and $\Delta=\pm180°$ (0 and $\pm\pi$ radians) and may thus yield inaccurate results for measurements near these values of $\Delta$, e.g., gate oxide measurements.

When the ellipsometer employs the optional compensator (C), e.g., in the RCE arrangement, both cos $\Delta$ and sin $\Delta$ can be used to determine $\Delta$. Exemplary RCE arrangements and convenient measurement techniques are taught by U.S. Pat. No. 6,831,743 to Aspnes et al. and by U.S. Pat. No. 7,304,737 to Liphardt et al. Unfortunately, the extraction of $\Delta$ from cos $\Delta$ and sin $\Delta$ is frequently complicated, since four Fourier coefficients have to be taken into account in this case. Furthermore, optical alignment becomes more complicated. All of these factors tend to compound errors in the final measurement.

Before moving on, it should be noted that U.S. Pat. No. 5,181,080 and "A novel technique for performing ellipsometric measurements in a sub-micrometer area", SPIE Vol. 2004 Interferometry VI: Applications, 1993, pp. 313 both by Fanton et al. describe a beam profile ellipsometry (BPE) approach that is well-suited for thickness measurements. In fact, this approach is related to the beam-profile reflectometry (BPR) method of Gold et al. taught in U.S. Pat. No. 4,999,014.

Spectroscopic Ellipsometry, Polarimetry and Related Methods

Ellipsometry is enhanced by extending the range of wavelengths of electromagnetic radiation impinging on the sample to yield spectroscopic ellipsometry. Such broadband or multi-wavelength ellipsometric techniques are practiced in many embodiments, among them in those employing a continuously rotating compensator and a step-wise rotating or a fixed compensator in the RCE arrangement.

Continuously rotating compensators are used in U.S. Pat. No. 6,449,043 by Aspnes et al. Their broadband spectroscopic rotating compensator ellipsometer rotates the compensator at an angular frequency $\omega$. The detector signal is analyzed at frequency components $2\omega$, $4\omega$. Thus, one obtains Fourier coefficients corresponding to $2\omega$ and $4\omega$. Another example of spectroscopic ellipsometry using a compensator rotating at w is found in U.S. Pat. No. 6,982,791 to Opsal, who teaches measurement of critical dimensions and thin film properties. Continuously rotating compensator is also used by Opsal et al., "Broadband spectral operation of a rotating-compensator ellipsometer", Thin Solid Films, Vol. 313-314, 13 Feb. 1998, pp. 58-61 to operate over a wide spectral range spanning from 200 to 800 nm. Other examples are provided by Johs et al, in U.S. Pat. No. 5,872,630 and by Aspnes et al, in U.S. Pat. No. 6,650,415. The latter reference teaches an advanced broadband spectroscopic ellipsometer in which compensator phase retardation is near 180° and sufficiently near at least 90° or 270° or in a range from 90° to 180°. A still different embodiment employing two rotating compensators at distinct angular frequencies, e.g., $5\omega$, $3\omega$, etc., is taught by Joungchel Lee et al, in "Dual rotating-compensator multi-channel ellipsometer: Instrument development for high-speed Mueller matrix spectroscopy of surfaces and thin films", Review of Scientific Instruments, Vol. 72, 1742 (March 2001).

RCE with a rotating compensator can be practiced in various geometries, including at normal incidence. For example, a simple, normal incidence rotating compensator RCE is taught in U.S. Pat. No. 7,355,708 to Aspnes. In a further improvement, U.S. Pat. No. 5,757,494 to Green et al. teaches data acquisition at other than principal or Brewster angles of incidence in a spectroscopic ellipsometer. Another way to handle incidence angles in spectroscopic ellipsometry involves a concave mirror and is described in U.S. Pat. No. 7,489,399 to Lee. Still more teachings on the types of optics trains that can be used in RCE systems can be found in U.S. Pat. Appl. 2006/0268272 to Liphardt et al.

Now, step-wise rotation of the compensator, e.g., as taught by Johs in U.S. Pat. No. 7,075,649, is employed to effect a plurality of sequentially discrete, rather than continuously varying polarization states during data acquisition. Such arrangement usually obtains calibration data at several of these discrete polarization settings. Another broadband spectroscopic RCE disclosed in U.S. Pat. No. 7,193,710 to Johs et al. specifically states that continuous or step-wise rotation is permitted. Furthermore, this method can be extended to RCE, RPE and RAE arrangements. In a still more recent reference, namely U.S. Pat. No. 7,492,455, Johs applies the teaching to non-rotating (fixed) elements during data collection.

In diffracting structures film thickness and index n of films under the structure can be found by spectroscopic reflectometry, as discussed in the section on spectroscopy, or by spectroscopic ellipsometry. Either method uses polarized broadband radiation to obtain an intensity or ellipsometric signature of the diffracting structure. This signature is matched with a database to determine grating shape parameters of the structure. Note that a spectroscopic scatterometer can be used for spectroscopic ellipsometry or reflectometry. For teaching relating scatterometry to critical dimension measurements in particular see U.S. Pat. Nos. 6,483,580; 5,963,329; 6,429,943 and 6,483,580. Furthermore, as integrated circuits move to 22 nm and 18 nm nodes, it becomes more desirable to obtain all four Stokes parameters during an optical critical dimensions (OCD) measurement in order to measure the small CD and shallow trench accurately. For more details the reader is referred to R. Silver et al., "Fundamental Limits of Optical Critical Dimension Metrology: A Simulation Study", Proc. Of SPIE, Vol. 6518 65180U-1, 2007.

In parallel with the above teachings, it should be noted that in U.S. Pat. No. 7,286,243 Rosencwaig improves on BPR (beam profile reflectometry) and BPE (beam profile ellipsometry) by combining them into spectroscopic BPR+BPE. He uses a wide range of angles of incidence $\theta_i$ while in overall normal incidence focus mode. Thus, there is a spread of angles of incidence $\theta_i$ with respect to the surface of the sample. His teachings are particularly useful for measuring thin film thickness t, critical dimensions and indices n, k. His apparatus is also suitable for obtaining Fourier components.

Spectroscopic polarimetry is in some sense more rigorous than broadband spectroscopic ellipsometry and is typically used to characterize the full Mueller matrix of optical components and entire optical systems. A full-fledged method for determining the Mueller matrix from spectroscopic polarimetry is taught by Otani et al., "Spectroscopic Mueller matrix polarimeter using four channeled spectra", Frontiers in Optics, Optical Society of America Technical Digest, 2008. Otani's approach requires four shots at specific settings of polarizing optics and the use of quarter wave plates as polarizing and analyzing optics. The plates rotate synchronously at $\omega$ and $5\omega$.

A still more recent method for spectroscopic polarimetry is taught by Okabe et al., "Spectroscopic polarimetry using channeled spectroscopic polarization state generator (CSPSG)", Optics Express, Vol. 15, No. 6, 19 March, 2007 pp. 3039. This approach uses no moving parts and allows the operator to characterize the full Mueller matrix with four (4) channels. A general arrangement for CSPSG and its direct relation to the Stokes vector S whose components $\{S_0, S_1, S_2, S_3\}$ are expressed in terms of wave number k (inversely related to wavelength $\lambda$) is illustrated in FIG. 2A. Note that in order to obtain good results, the two compensators, here implemented by retarders $R_1$ and $R_2$, are very thick. In fact, thicknesses $D_1$ and $D_2$ are required to be "fairly thick" such that the ranges of retardations over the spectral bandwidth of interest are much larger than $2\pi$. The same is expressly stated by K. Oka and T. Kato, "Static Spectroscopic Ellipsometer Based on Optical Frequency-Domain Interferometry," *Polarization Analysis and Measurement IV*, D. H. Goldstein, D. B. Chenault, W. G. Egan, and M. J. Duggin, eds., Proc. SPIE 4481, 2001, pp. 137-140.

The reason for such large thicknesses and correspondingly large variation in retardation as a function of wave number k (or wavelength $\lambda$) over the spectral range is due to the need for a highly oscillatory "channeled spectrum", also referred to as the "finely-vibrating spectrum". FIG. 2B illustrates the second Stokes parameter $S_2(k)$ and its finely-vibrating spectrum as a function of k for the CSPSG of FIG. 2A. In this configuration, the radiation emerging from the CSPSG is elliptically polarized and its state of polarization varies rapidly with k over the broadband spectral range due to the effect of the finely-vibrating spectrum.

The major problem with such channeled spectropolarimetry has been its low stability, owing to the fact that high-order retarders, such as $R_1$ and $R_2$, are generally susceptible to various kinds of perturbations. These not only include perturbations due to temperature, but also other operating factors.

Clearly, the numerous techniques that combine aspects of spectroscopy and broadband ellipsometry have yielded many useful instruments for optical characterization. Several of them offer the ability to measure very thin films and to determine indices n, k. The most complex among them, such as spectropolarimeters and CSPSG in particular, even allow a complete characterization of the system and sample in terms of full-fledged Mueller matrices. However, frequently such level of analysis is unnecessary. Rather, a cost-effective and reliable method to measure film thickness t, characterize critical dimensions or trench depth in periodic structures as well as determine the complex coefficients n, k is the main objective. In addition, it would be advantageous to obtain the full Stokes vectors with the same apparatus.

Objects and Advantages

In view of the above prior art limitations, it is an object of the invention to provide an apparatus and a method for practicing a combination of broadband spectroscopy and ellipsometry called phase-compensated sensitivity-enhanced spectroscopy (PCSES). The objective of PCSES is to combine the advantageous aspects of broadband ellipsometry and spectrometry to derive a better system to cost-effectively and reliably measure thin film thickness t down to zero.

PCSES also aims to streamline characterization of critical dimensions and determination of trench depth in periodic structures.

In addition, PCSES is intended to provide the full Stokes parameters that are increasingly more important in examining critical dimensions in next generation integrated circuits (ICs).

Furthermore, it is an object of the invention to ensure that PCSES can be practiced with a low-cost and highly reliable apparatus that is easy to align and calibrate.

These and other objects and advantages of the invention will become apparent from the ensuing description.

SUMMARY OF THE INVENTION

The objects and advantages of the invention are secured by a novel method that convolves spectroscopic data with certain phase information for practicing phase-compensated sensitivity-enhanced spectroscopy (PCSES). The method calls for deriving a beam of radiation in a polarization state $PS_p$ from a source emitting at a plurality of wavelengths, and placing in the beam a compensator capable of altering polarization state $PS_p$ by applying a delimited phase shift $\Delta$ between two orthogonal polarization axes of the radiation to restrict a finely-vibrating spectrum. A sample is disposed in the beam after the compensator to generate a response beam by reflection, transmission or even both. A polarization state $PS_a$ of the response beam is passed to a detector to measure a spectrum of the response beam that is in polarization state $PS_a$. Now, a first spectrum is collected when polarization states $PS_p$, $PS_a$ and the compensator are in a first polarization-altering configuration. A second spectrum is collected when polarization states $PS_p$, $PS_a$ and the compensator are in a second polarization-altering configuration. A phase-compensated spectrum is derived from the first and second spectra. The derivation may involve any operation ranging from examining both spectra side-by-side to combining them in accordance with any combinatorial procedure.

The polarization-altering configurations are set by the type of alignment of the polarization states $PS_p$, $PS_a$ and of a principal axis (i.e., the ordinary axis associated with refractive index $n_o$ or the extraordinary axis associated with refractive index $n_e$) of the compensator. In one embodiment, the first polarization-altering configuration is achieved by aligning polarization states $PS_p$, $PS_a$ and a principal axis of the compensator, while the second polarization-altering configuration is obtained through non-alignment of the polarization states $PS_p$, $PS_a$ and a principal axis of the compensator. For example, one convenient non-alignment is accomplished by rotating the principal axis of the compensator by 45° with respect to the first polarization-altering configuration. In this case polarization states $PS_p$, $PS_a$ remain aligned.

In a preferred embodiment, polarization state $PS_p$ is produced by a polarizing mechanism set at a rotation angle P, the polarization state $PS_a$ is produced by a polarizer or analyzer set at a rotation angle A, and the compensator is set at a rotation angle $C_1$. The polarizing mechanism can be a polarizer, especially when using a source that emits unpolarized radiation. Further, a supplementary compensator set at a rotation angle $C_2$ can be placed in the response beam before the analyzer.

The four angles P, A, $C_1$, $C_2$ define the polarization-altering configurations. Although there are many conventions for defining angles P, A, $C_1$, $C_2$, it is most convenient to measure them with respect to a plane of incidence PI containing the beam incident on the sample and the response beam generated by the sample. Usually, the angle of incidence $\theta_i$ of the beam will be in a range from 7° to 75°. Furthermore, the most useful values for setting rotation angles P, A, $C_1$ and $C_2$ for the first and second polarization-altering configurations as well as any other polarization-altering configurations include 0°, 45°, 90°, −45° and integer multiples thereof.

In one particularly preferred embodiment, the rotation angles for the first phase-altering configuration are set as follows: P=−A=C=45°. Meanwhile, the rotation angles for the second phase-altering configuration are: P=−A=45°, C=0°. This choice is advantageous because the first and second spectra are then described by simple mathematical expressions. Namely, the first spectrum is expressed as:

$$R_s + R_p - 2\sqrt{R_s R_p} \cos \delta,$$

while the second spectrum is expressed as:

$$R_s + R_p - 2\sqrt{R_s R_p} \cos(\Delta+\delta),$$

where $\delta$ is the phase difference between $r_p$ and $r_s$, $R_s = |r_s|^2$, $R_p = |r_p|^2$ and the delimited phase shift $\Delta$ results from an effective polarization-altering contribution of the combination of $C_1$ and $C_2$. The phase-compensated spectrum T derived from the first and second spectra in this preferred embodiment is a ratio defined as:

$$T = \frac{R_s + R_p - 2\sqrt{R_s R_p} \cos(\Delta+\delta)}{R_s + R_p - 2\sqrt{R_s R_p} \cos\delta}.$$

In another embodiment, the first and second polarization-altering configurations are: P=45°, A=45°, C=0° and P=45°, A=45°, C=90° so that the first spectrum is:

$$T=\frac{1}{4}[R_s+R_p+2\sqrt{R_s R_p}\cos(\Delta+\delta)],$$

and the second spectrum is:

$$T=\frac{1}{4}[R_s+R_p+2\sqrt{R_s R_p}\cos(\Delta-\delta)].$$

In still another embodiment, the first and second polarization-altering configurations are: P=45°, A=−45°, C=0° and P=45°, A=−45°, C=90°, so that the first spectrum is:

$$T=\frac{1}{4}[R_s+R_p-2\sqrt{R_s R_p}\cos(\Delta+\delta)],$$

and the second spectrum is:

$$T=\frac{1}{4}[R_s+R_p-2\sqrt{R_s R_p}\cos(\Delta-\delta)].$$

The delimited phase shift $\Delta$ of the compensator introduces a periodicity into the response beam that is characterized by a finely-vibrating spectrum. The finely-vibrating spectrum is related to delimited phase shift $\Delta$ and the total bandwidth of the radiation emitted by the source. To practice the invention, phase shift $\Delta$ needs to be controlled in a predetermined manner; specifically it should be adjusted to restrict the finely-vibrating spectrum with respect to a spectral bandwidth SBW of the detector such that:

$$\frac{d\Delta}{d\lambda} \cdot SBW \ll \pi.$$

Moreover, phase shift $\Delta$ should preferably be limited to between 0° and 360° or to just a few 360° cycles (e.g., less than 50) over the plurality of wavelengths emitted by the source.

In some embodiments of the method additional spectra can be collected and used for deriving the phase-compensated spectrum. For example, a third spectrum is collected when polarization states $PS_p$, $PS_a$ and the compensator are in a third polarization-altering configuration and the phase-compensated spectrum is derived from the first, second and third spectra. Beyond that, at least one more supplementary spectrum can be collected when the polarization states $PS_p$, $PS_a$ and said compensator are in at least one corresponding polarization-altering configuration. The phase-compensated spectrum is then derived from the first, second, third and one or more supplementary spectra. It should be noted, that with just one supplementary spectrum it is possible to derive a ellipsometric measurement of the sample in terms of the Stokes vector. More spectra can provide sufficient information to solve the complete ellipsometric equations, e.g., the Mueller matrices or other equivalent mathematical formulations, and determine the relevant polarizations and phases of the radiation.

The plurality of wavelengths emitted by the source can span a significant portion of the optical spectrum and much beyond. The coverage can be discontinuous or continuous. Preferably, the wavelengths cover a continuous range rather than very specific spectral values. For example, the wavelengths can span a continuous spectral range from vacuum-ultra-violet (VUV) to infra-red (IR).

The invention further extends to an apparatus for practicing phase-compensated spectroscopy. The apparatus has a source that emits at a plurality of wavelengths and is used for deriving a beam of radiation in a polarization state $PS_p$. A compensator is placed in the beam for altering the polarization state $PS_p$ by applying a delimited phase shift $\Delta$ between two orthogonal polarization axes of the radiation that restricts a finely-vibrating spectrum. A sample is disposed in the beam after the compensator to generate a response beam, and an analyzer is placed in the response beam for passing a polarization state $PS_a$ thereof. A detector disposed in the response beam after the analyzer measures a spectrum of the response beam and communicates it to a computing unit. The latter collects a first spectrum when polarization states $PS_p$, $PS_a$ and the compensator are in a first polarization-altering configuration, and a second spectrum when polarization states $PS_p$, $PS_a$ and the compensator are in a second polarization-altering configuration. The unit then derives a phase-compensated spectrum from the first and second spectra thus collected.

The source has a polarizing mechanism set at a rotation angle P for enforcing polarization state $PS_p$. This polarizing mechanism may be inherent in the source, integrated with the source or a separate mechanism, such as a polarizer. The last solution is required when the source emits unpolarized radiation. Meanwhile, the compensator is set at a rotation angle $C_1$ and the analyzer is set at a rotation angle A for enforcing polarization state $PS_a$. In some embodiments a supplementary compensator is disposed in the response beam before the analyzer and set at a rotation angle $C_2$. Thus, rotation angles P, A, $C_1$, $C_2$ define the polarization-altering configurations. It should be noted that in the absence of the supplementary compensator, the polarization-altering configurations are defined by just P, A and $C_1$. Whether three or four rotation angles make up the polarization-altering configuration, it is once again convenient to define them with respect to a plane of incidence PI containing the beam incident on the sample and the response beam generated by it. Preferably, the sample is disposed such that an angle of incidence $\theta_i$ of the beam measured with respect to a normal to the sample's surface remains in a range from 7° to 75°.

The compensator can be any suitable device that operates by introducing delimited phase shift Δ between orthogonal polarizations of the emitted radiation. These devices include: single wave plates, multiple wave plates, prisms, retarders, Berek plates and Fresnel rhombs among others. The physical parameters of the compensator are selected so as to limit phase shift Δ as required for practicing the invention; namely restrict the finely-vibrating spectrum. For example, when the compensator is a multiple order wave plate this is accomplished by confining its thickness D to a range from 0.1 to 0.5 mm. It should be further recognized that the compensator can be made of any suitable materials including $MgF_2$ and $SiO_2$.

As remarked above, the plurality of wavelengths preferably spans a continuous range from VUV to IR. This may be achieved by using scanning sources or broadband sources, including compound sources. Depending on the apparatus, broadband compatible optics should be used; for example, off-axis parabolic mirrors can be employed for collimating the beam, the response beam or both. In the same vein, a toroidal reflector can be relied upon to image the source to any aperture that the apparatus may require.

Of course, the method and apparatus of invention can be embodied in many different ways. A detailed description of the preferred embodiments of the invention presented below in reference to the appended drawing figures will elucidate these embodiments and extensions thereof.

BRIEF DESCRIPTION OF THE DRAWING FIGURES

FIG. 10b is a top plan view of a part belonging to the detector of FIG. 10a.

Figure 13A:
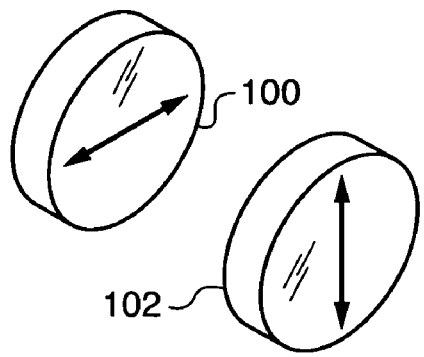
Figure 13B:
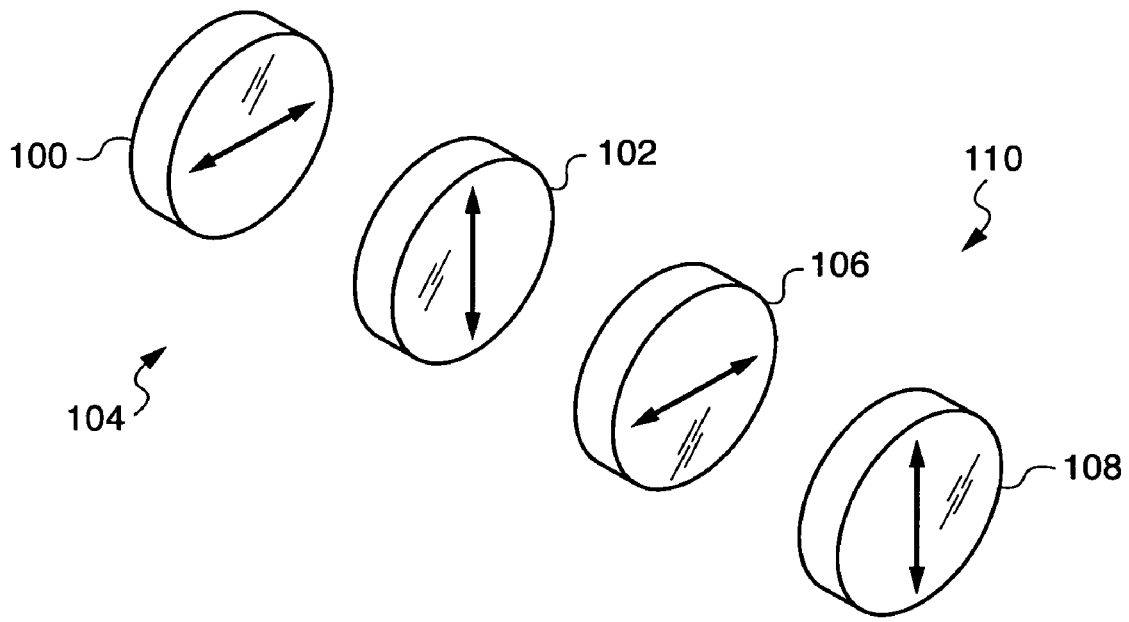
Figure 13C:
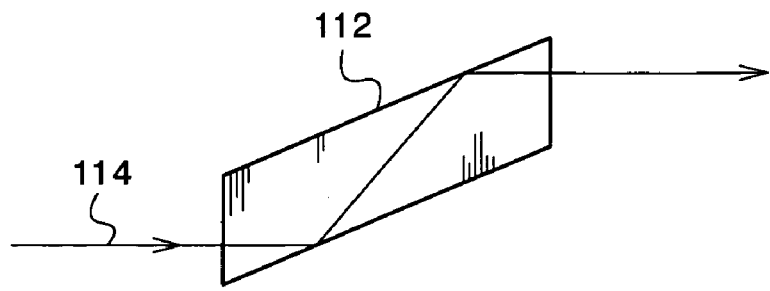

FIGS. 13a-c show several different configurations of retardance elements that can be employed to construct compensators suitable for apparatus according to the invention.

Figure 14:
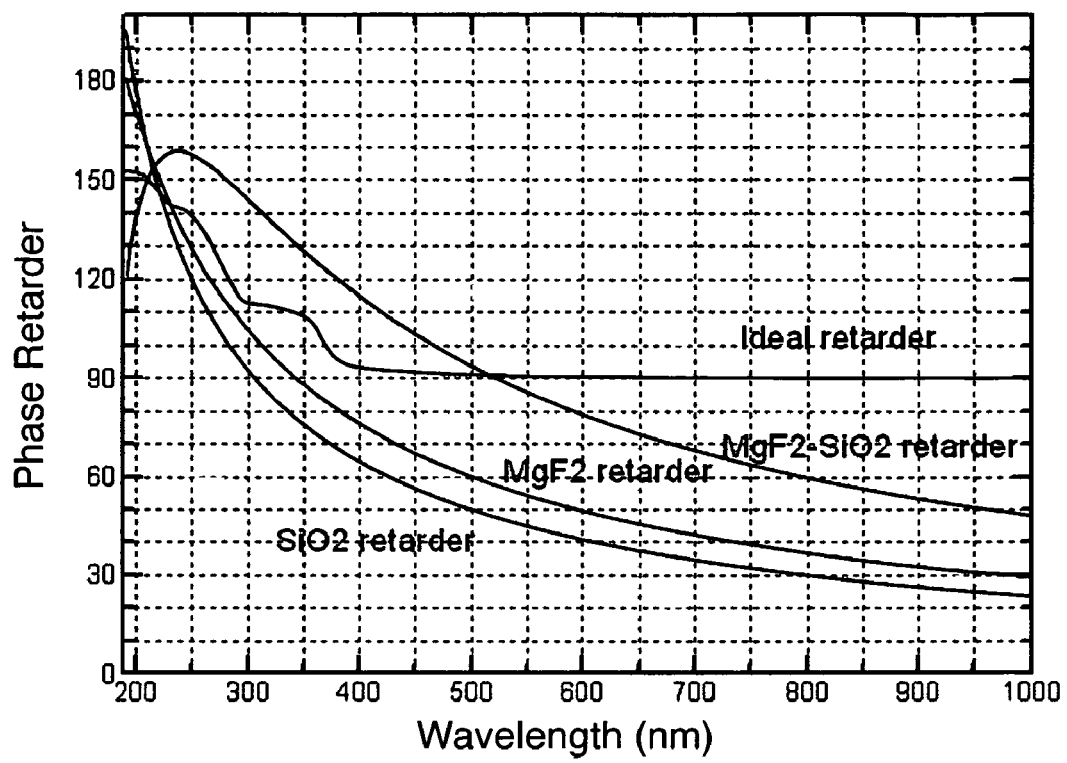

FIG. 14 shows an example of "ideal" retardance vs. wavelength curve compared with the character of several exemplary compensator designs as shown in FIGS. 13a-c.

Figure 15:
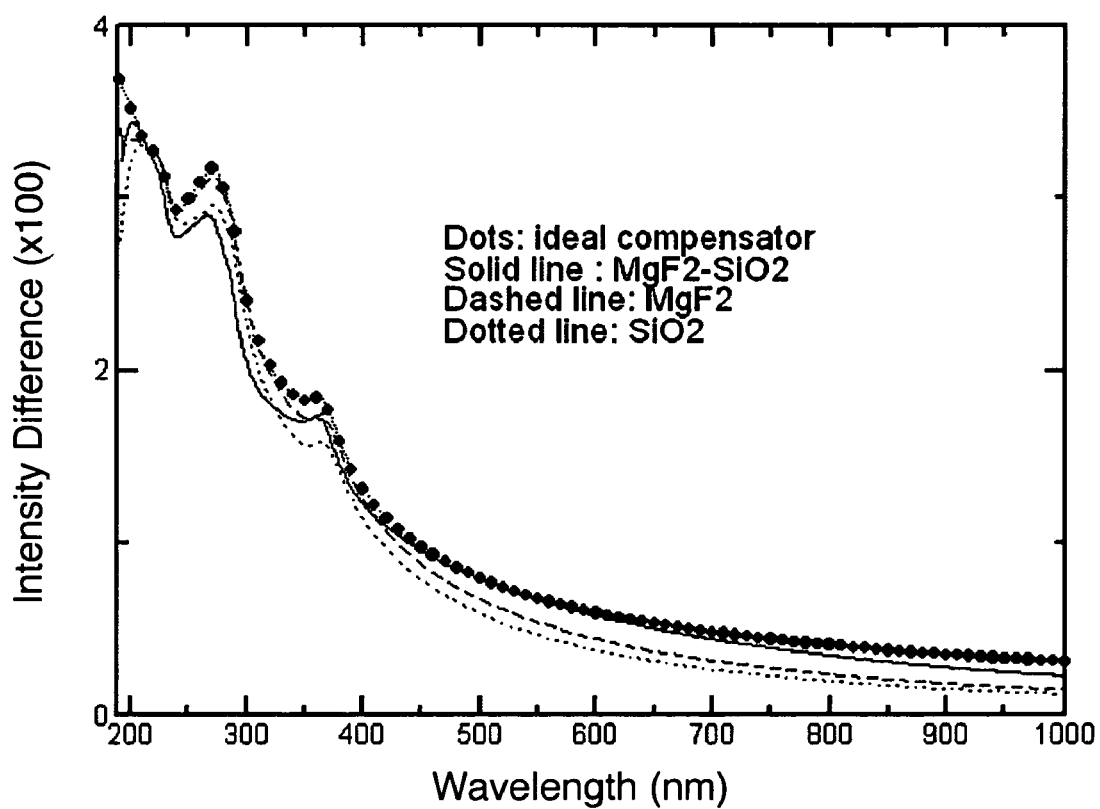

FIG. 15 shows measurement sensitivity provided by embodiments of the invention employing the compensator designs of FIGS. 13a-c.

Figure 16A:
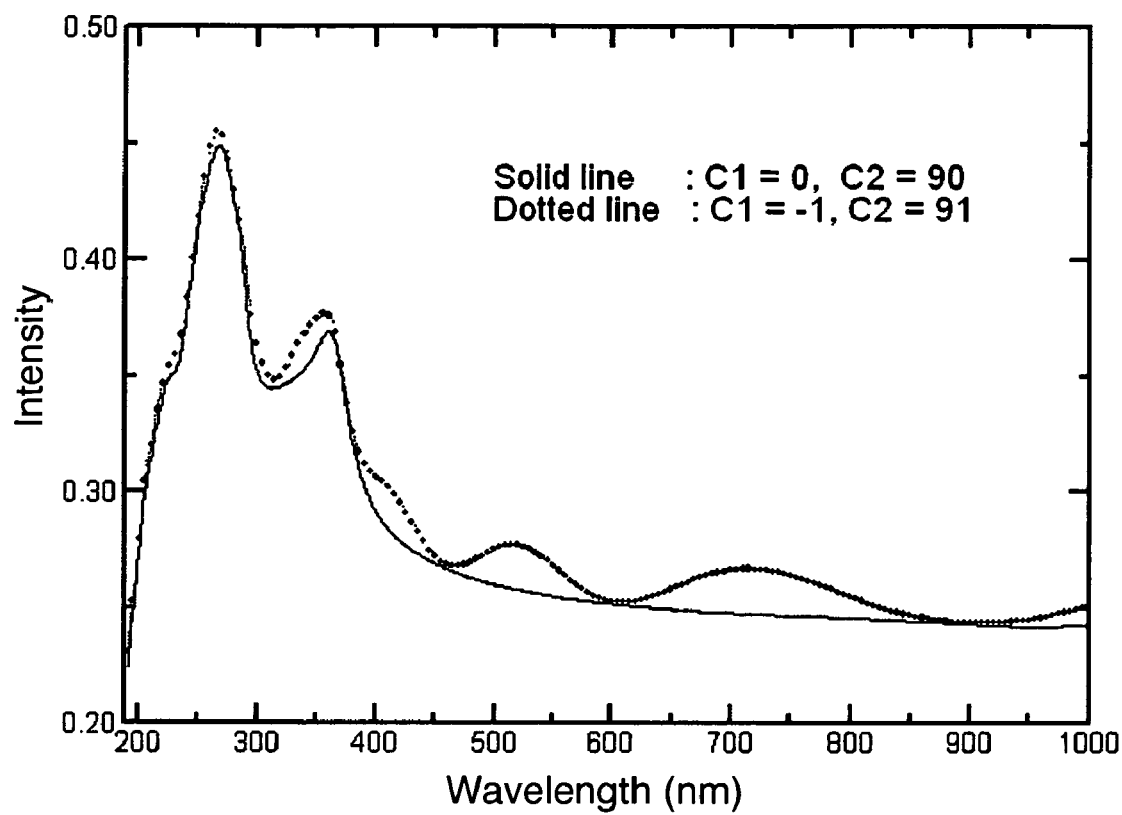
Figure 16B:
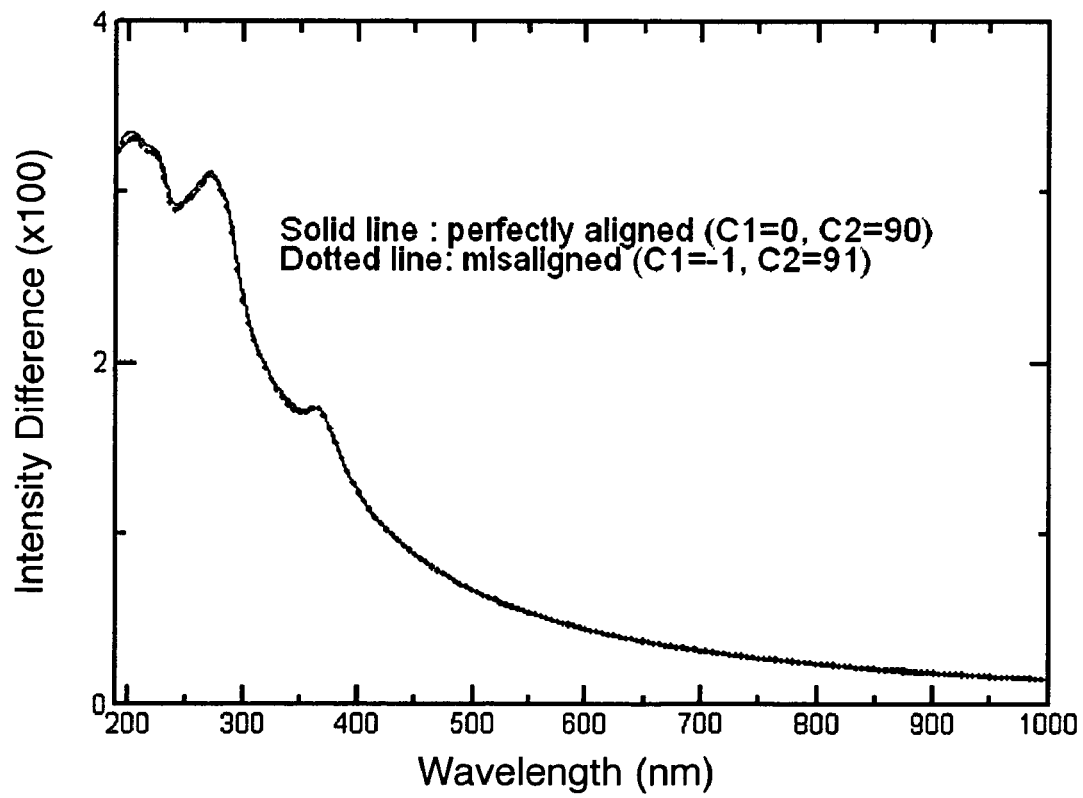

FIGS. 16a-b are graphs of phase behavior and characterization sensitivity for embodiments with slightly misaligned compensators, as may happen in practice.

Figure 17:
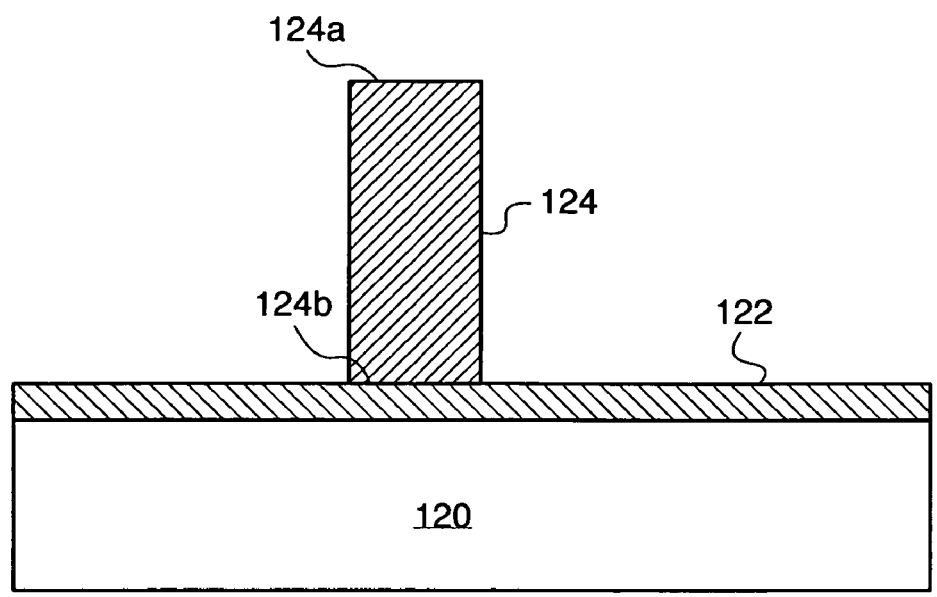

FIG. 17 is a side view illustrating a portion of a sample whose critical dimensions (CDs) can be examined by phase-compensated spectroscopy.

Figure 18:
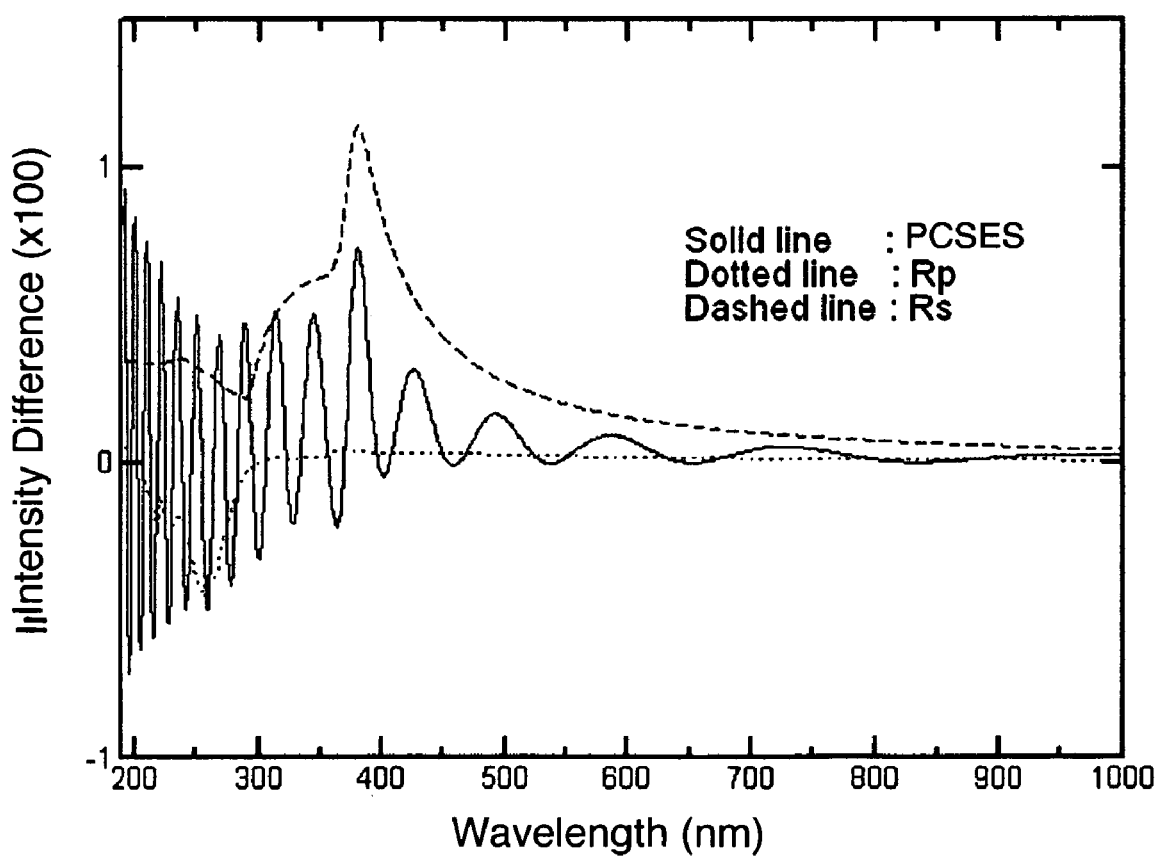

FIG. 18 is a graph of spectra collected from the sample of FIG. 17.

DETAILED DESCRIPTION

This invention presents a novel method and correspondent apparatus for optical characterization of samples. The method builds on aspects of spectrometry in combination with select aspects of broadband ellipsometry. Specifically, the method teaches a way of convolving spectroscopic data with a very limited amount of phase information to practice phase-compensated sensitivity-enhanced spectroscopy (PCSES). In its basic modes, phase information required by PCSES may or may not be sufficient to practice ellipsometry.

PCSES relies on the novel and surprising finding that convolving spectroscopic data with an amount of phase information that would be assumed inadequate for useful analysis permits one to practice high quality optical characterization. The type and manner of collecting the phase information, as well as the setting of certain parameters of the apparatus are crucial to proper implementation of the novel method. For one, in contrast with CSPSG as applied to spectroscopic ellipsometry and discussed in the background section, rather than using "fairly thick" birefringent retarders that produce ranges of retardations over the spectral bandwidth of interest that are much larger than 2π, the invention uses a thin retarder or compensator. In particular, the compensator introduces a delimited phase shift Δ between the orthogonal polarization axes to restrict a finely-vibrating spectrum that arises due to the fact that retardation varies as a function of wavelength λ. In practical applications, this means that the compensators used in the apparatus of invention are just on the order of about 0.1 to 0.5 mm, while conventional CSPSG employs retarders of thickness ranging from 10 to 40 mm.

Because of the extensive nature of the teachings required to enable the practice of PCSES, the detailed description will be presented in several parts. The description is intended not only to provide the best mode, but also to teach a person skilled in the art how to implement PCSES in various situations.

Description of Basic Apparatus and Method

Figure 1:
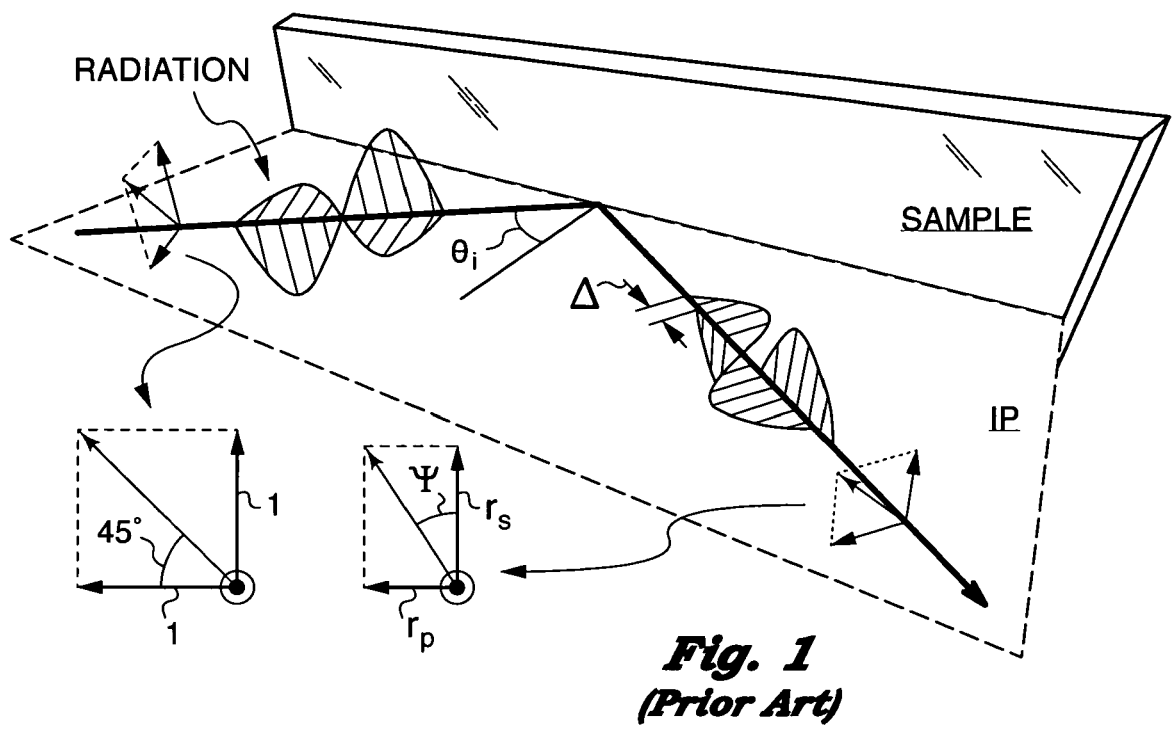
FIG. 1 (Prior art) is a perspective diagram illustrating the definitions of ellipsometric angles Δ and ψ.
Figure 2A:
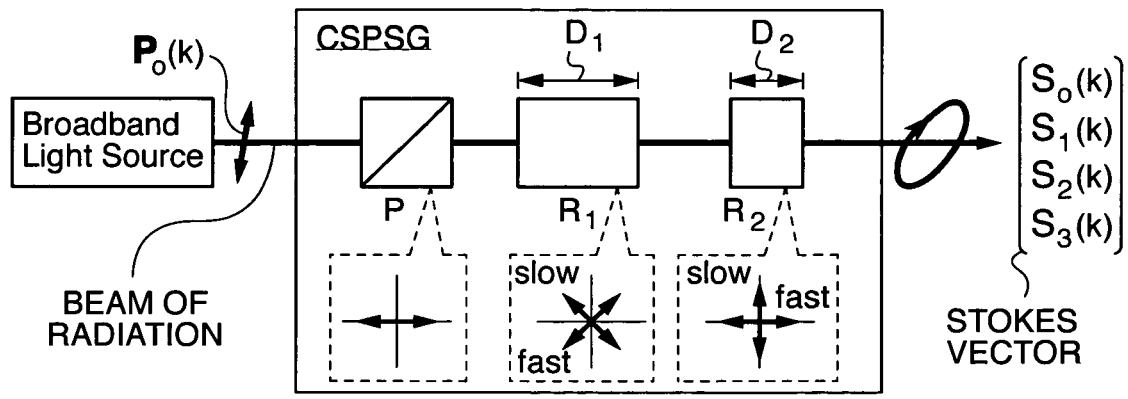
FIG. 2A (Prior art) is a plan diagram of a CSPSG apparatus in a typical configuration.
Figure 2B:
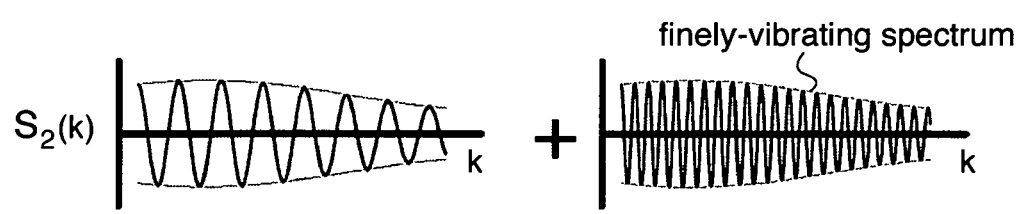
FIG. 2B (Prior art) is a graph showing the effect of a finely-vibrating spectrum produced by the CSPGS apparatus of FIG. 2A on the third Stokes parameter $S_2(k)$.
Figure 3:
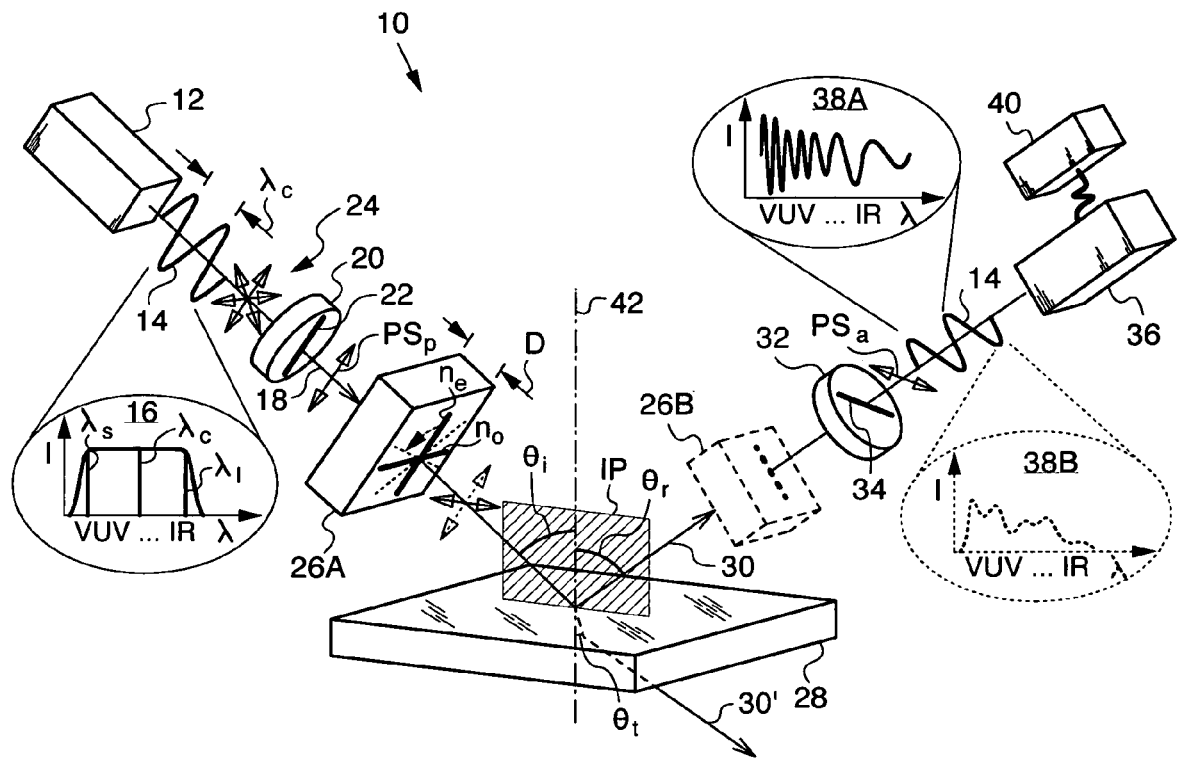
FIG. 3 is a three-dimensional diagram illustrating an apparatus for practicing phase-compensated sensitivity-enhanced spectroscopy (PCSES) in accordance with the invention.

The important aspects of an apparatus 10 designed to practice the method of invention are shown in a three-dimensional diagram in FIG. 3. Apparatus 10 has a source 12 that emits radiation 14 at a number of wavelengths λ. In particular, source 12 emits radiation 14 over a continuous and broadband spectral range 16 from vacuum-ultra-violet (VUV) to infra-red (IR). Of course, this typical range from about 100 nm to about 1,000 nm can be extended into shorter and longer wavelengths if deemed necessary. Also, with wavelengths below about 190 nm a vacuum chamber (not shown) may need to be used to avoid undue environmental absorption of radiation 14. Some specific wavelengths $\lambda_s$, $\lambda_c$ and $\lambda_l$ of radiation 14 are indicated in the diagram. It should be noted that spectral range 16 can be efficiently obtained by combining two or more suitable sources into a compound source, as will be appreciated by those skilled in the art. Alternatively, a scanning source such as a laser can be used.

Source 12 produces a beam 18 of radiation 14 that propagates in the direction indicated by corresponding arrows. Optical elements such as lenses, apertures, reflectors, etc. can be used to properly condition radiation 14 into beam 18. These optical elements are not shown, but are understood by those skilled in the art of broadband spectroscopy or ellipsometry.

Source 12 has a polarizing mechanism 20 for enforcing a polarization $PS_p$ on radiation 14 making up beam 18. In the present embodiment, polarizing mechanism 20 is a separate mechanism in the form of a polarizer whose polarization axis 22 passes light in linear polarization state $PS_p$ that is parallel with axis 22. In general, any polarizing mechanism capable of deriving beam 18 in polarization state $PS_p$ while blocking or deflecting polarization orthogonal to $PS_p$ is admissible. Certain sources have polarizing mechanisms that are inherent to them (e.g., certain lasers) or are integrated with them. Such sources emit radiation 14 that is intrinsically polarized and may not require any external polarizers. In contrast, source 12 emits unpolarized radiation 14. This is indicated by an unpolarized state 24 of radiation 14. Therefore, polarizer 20 is required to derive beam 18 in polarization state $PS_p$.

Figure 4:
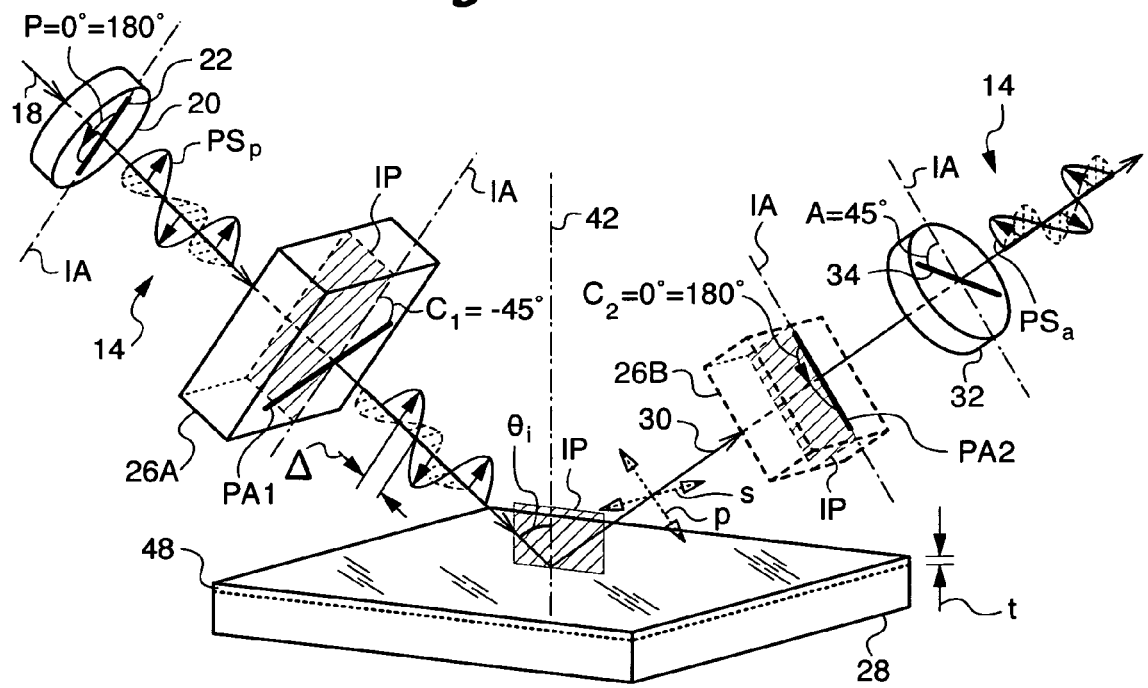
FIG. 4 is a three-dimensional diagram illustrating in more detail a portion of the apparatus of FIG. 3.

A compensator 26A is placed in beam 18 for altering polarization state $PS_p$ by applying a delimited phase shift Δ between the two orthogonal polarizations of radiation 14 (explicitly shown in FIG. 4.) The wavelength-dependence of delimited phase shift Δ is sufficiently small to restrict a finely-vibrating spectrum over spectral range 16 employed by apparatus 10 as further explained below. Suitable devices that can serve as compensator 26A include: single wave plates, multiple wave plates, prisms, retarders, Berek plates, Fresnel rhombs and any other passive or active devices. The physical parameters of the compensator are selected to delimit phase shift Δ as required for practicing the invention. In the present embodiment, compensator 26A is a multiple order wave plate made of $MgF_2$ and its thickness D is chosen within a range of 0.1 to 0.3 mm.

A sample 28 is disposed in beam 18 after compensator 26A to generate a response beam 30. Although in the present embodiment response beam 30 under consideration is produced by reflection, it is also possible to use response beam 30' produced by transmission, or even to utilize both response beams 30, 30'. A person skilled in the art will appreciate that corresponding optics need to be put in place to intercept and guide transmitted response beam 30'.

An analyzer 32 is placed in response beam 30 for passing a polarization state $PS_a$ of response beam 30. Analyzer 32 is a polarizing mechanism that has a polarization axis 34 and passes radiation or light in linear polarization state $PS_a$ that is parallel with axis 34. Any polarizing mechanism capable of performing this function while blocking or deflecting radiation 14 in a polarization state orthogonal to $PS_a$ can be employed as analyzer 32.

A detector 36 is disposed in response beam 30 after analyzer 32. Detector 36 is designed to measure the spectra of response beam 30 at different times. Since these spectra cover a broad range of wavelengths that correspond to spectral range 16 of radiation 14 originally emitted by source 12, it is important that detector 36 be sensitive over that range. Furthermore, delimited phase shift Δ restricts a periodicity of the finely-vibrating spectrum and thus affects the spectrum of radiation 14 in polarization state $PS_a$ making up response beam 30 that arrives at detector 36. This periodicity, in turn, impacts optical resolution and spectral bandwidth SBW requirements of detector 36 as described in more detail below. In view of these exigencies, detector 36 should have a sufficiently high optical resolution and fully cover the spectral range in order to be well-matched to the task.

A spectrometer whose range extends from VUV to near IR with a dispersion grating capable of resolving ~3 nm wavelength differences or smaller is an appropriate choice. The diagram of FIG. 3 shows a first spectrum 38A and a second spectrum 38B of radiation 14 in polarization state $PS_a$ as measured by detector 36 at different times. In alternative embodiments that do not use a continuous spectral range 16 and instead emit and measure only a certain number of wavelengths, e.g., $\lambda_s$, $\lambda_c$ and $\lambda_l$, detector 36 can be a multi-channel analyzer.

Detector 36 is connected to a computing unit 40. The latter is designed to receive and perform operations on spectra, such as first spectrum 38A and second spectrum 38B measured by detector 36. For this purpose the connection between detector 36 and 40 is made over an efficient link to ensure rapid communication.

Apparatus 10 can utilize a supplementary compensator 26B disposed in response beam 30 before analyzer 32. The criteria for choosing the type and material of supplementary compensator 26B are analogous to those encountered in the choice of compensator 26A. Note that in an alternative embodiment compensator 26A can be used by itself at the location of optional compensator 26B without the latter. Still, although it is possible to practice the invention with just one compensator 26A, the use of supplementary compensator 26B permits more flexibility for reasons explained below. To understand the issues involved, it is important to first review the operational principles of compensators 26A, 26B.

Concentrating on compensator 26A, we see that it has two principal axes associated with its two different indices of refraction. In particular, it has an ordinary axis or "slow axis" associated with refractive index $n_o$ and an extraordinary axis or "fast axis" associated with refractive index $n_e$. These indices are used in FIG. 3 to label the two principal axes of compensator 26A. FIG. 3 also illustrates a way of defining an incidence plane IP, where beam 18 incident on sample 28 and response beam 30 generated by sample 28 are both contained in incidence plane IP. Under this definition, an angle of incidence $\theta_i$ of beam 18 measured with respect to a normal 42 to the surface of sample 28, as well as an angle of reflection $\theta_r$ of response beam 30 and an angle of refraction $\theta_t$ describing the transmission of response beam 30' through sample 28 are all contained in plane IP. Although other conventions are possible, referencing all principal axes rotations as well as polarization states with respect to plane IP is very convenient and shall be used throughout the remainder of the description. Thus, for example, the rotation of principal axes $n_o$, $n_e$ of compensator 26A occurs in a plane perpendicular to plane IP.

When beam 18 of radiation 14 is incident on sample 28, various rays within beam 18 have different angles of incidence on sample 28 if additional focusing element are included (not shown in FIG. 3). Although such variations are typically small with negligible effect on operation, it is still helpful to define angle of incidence $\theta_i$ of beam 18 as the angle the beam axis makes with respect to normal 42. Here, beam 18 and the beam axis are taken to have their ordinary meaning in the art of optics. In this manner, possible ambiguities introduced by any angular spread that may occur among rays within beam 18 can be avoided.

Consider two cases. In case one, beam 18 is collimated as it impinges on sample 28. In case two, beam 18 is focused onto sample 28 by placing a high-NA lens in its path. The beam angle of incidence $\theta_i$ for both cases is 30°, even though individual rays within beam 18 incident on sample 28 can impinge at angles other than 30°, especially in case two. If normal incidence (i.e., $\theta_i=0°$) is assumed in this example, then beam angle of incidence $\theta_i=0°$, even though rays within beam 18 in case two can have substantially non-normal angles of incidence (e.g., 45° or more) as measured to normal 42. Clearly, however, in embodiments of the invention, radiation 14 is incident on sample 28 in the form of beam 18 making non-normal beam angle of incidence $\theta_i$.

Selection of beam angle of incidence $\theta_i$ for phase-compensated spectroscopy is governed by the following considerations. As $\theta_i$ increases, the difference between $r_p$ and $r_s$ tends to increase, which is generally helpful for characterization. However, as $\theta_i$ increases, the spot size on sample 28 also increases, which can be detrimental to characterization, especially if sample 28 exhibits substantial lateral variation. Selecting appropriate angles of incidence $\theta_i$ for various specific cases in view of these principles is within the capability of those skilled in the art. Specifically, angle of incidence $\theta_i$ of beam 18 is preferably kept in a range from 7° to 75°. For thin film measurements $\theta_i$ preferably resides between 45° and 75°. For trench and critical dimension measurements $\theta_i$ should be near normal, i.e., near 7°. Preferably, beam 18 is collimated to achieve small spot size.

Referring to the details of apparatus 10 depicted in FIG. 4, we see where plane IP passes through compensator 26A. Compensator 26A has a principal axis PA1 which is chosen to be the extraordinary axis $n_e$ or "fast axis" for the purposes of the present invention. Principal axis PA1 is set at a rotation angle $C_1$ with respect to an axis IA that defines the intersection between plane IP and the perpendicular plane that contains rotation angle $C_1$ of compensator's 26A principal axis PA1. A rotation angle P of polarization axis 22 belonging to polarizer 20 that enforces polarization state $PS_p$ on beam 18 is similarly defined with respect to plane IP. The same is true for a rotation angle A of polarization axis 34 of analyzer 32 in charge of passing polarization state $PS_a$ of radiation 14 in response beam 30. Finally, a rotation angle $C_2$ of a principal axis PA2 (i.e., the "fast axis") of supplementary compensator 26B is defined with respect to incidence plane IP in the same manner. Together, rotation angles P, A, $C_1$, $C_2$ define a polarization-altering configuration of apparatus 10. It should be noted that in the absence of supplementary compensator 26B, the polarization-altering configuration is defined by rotation angles P, A and $C_1$ only.

As remarked above, compensator 26A is a device that introduces delimited phase shift $\Delta$ between orthogonal polarizations s and p of radiation 14 making up beam 18. Meanwhile, in accordance with a standard convention, polarization axes 22 and 34 of polarizer 20 and analyzer 32 respectively are aligned with the polarization as defined by the oscillation of the electric field of radiation 14. Differently put, polarization states $PS_p$ and $PS_a$ select the plane of oscillation of the E-field vector of radiation 14.

Now, the magnitude of delimited phase shift $\Delta$ caused by compensator 26A depends on its thickness D, the difference between the values of indices $n_e$ and $n_o$ and wavelength $\lambda$ of radiation 14. The complete relationship can be expressed as:

$$\Delta = \frac{2\pi(n_e - n_o)D}{\lambda}. \tag{Eq. 1}$$

In order for delimited phase shift $\Delta$ to restrict the finely-vibrating spectrum, as intended by the present invention, the periodicity of $\Delta$ over spectral range 16 has to be limited. More precisely, the maximum change in shift $\Delta$, or $\Delta_{max}$ from the shortest wavelength $\lambda_s$ to the longest wavelength $\lambda_l$, as indicated in FIG. 3, should be at one or just a few periods or multiples of 360° or $2\pi$. In other words:

$$\Delta_{max} = \Delta(\lambda_l) - \Delta(\lambda_s) \leq 2\pi m, \tag{Eq. 2A}$$

where m is a small integer, preferably less than 50 when the wavelengths in spectral range 16 extend from about 190 nm to 1,000 nm. Once spectral range 16 is known, this delimiting condition on phase shift $\Delta$ can be guaranteed by a judicious choice of indices $n_e$, $n_o$ and thickness D. In a preferred embodiment this limitation is selected such that:

$$\frac{d\Delta}{d\lambda} \cdot SBW \ll \pi, \tag{Eq. 2B}$$

where SBW is the spectral bandwidth of detector 36. Now, the finely-vibrating spectrum introduced by shift $\Delta$ causes a corresponding rotation of the polarization state of radiation 14 in a plane perpendicular to incidence plane IP. In most cases:

$$SBW \cdot \frac{d\Delta}{d\lambda} < 0.1 \cdot \pi = 18°,$$

and a typical detector 36 has an SBW of about 1~5 nm. So, for a wavelength range from 190 nm to 1,000 nm, the total change in $\Delta$ should be $<\pi \times 81/(1~5)$. This corresponds to about 8~40 oscillations or cycles over the finely-vibrating spectrum.

Once it arrives in response beam 30 at analyzer 32, radiation 14 will either be passed in polarization state $PS_a$ or filtered out if in a state orthogonal to $PS_a$. Indeed, shift $\Delta$ would not be relevant if not for the filtering effect of analyzer 32 that only passes radiation 14 in polarization state $PS_a$ to detector 36.

Supplementary compensator 26B operates according to the same physical principles as described above. Its use enables the method of invention to exercise more control over the total phase shift $\Delta$ when necessary. For example, in some cases, better sensitivity at certain wavelengths λ of interest, e.g., at or near $\lambda_s$, $\lambda_c$ and $\lambda_l$, or portions of spectral range 16 can be obtained when both compensators 26A, 26B are employed in apparatus 10.

The method of invention will be explained based on apparatus 10 as shown in FIGS. 3 and 4, and then in reference to the diagram of FIG. 5. Although the description will focus on reflected response beam 30 for reasons of clarity, it is understood that it can be applied to transmitted beam 30' as well. In fact, spectra from both response beams 30, 30' can be used, provided that a corresponding analyzer and detector are placed in the path of transmitted response beam 30'. A separate or even the same computing unit 40 can be used in such embodiments.

One key and novel aspect of the method convolves spectroscopic data with phase information impressed on radiation 14 by polarizer 20, compensator 26A, optional supplementary compensator 26B and analyzer 32. More precisely, polarizer 20, compensators 26A, 26B and analyzer 32 set rotation angles P, A, $C_1$, $C_2$—or just P, A, $C_1$ in the absence of supplementary compensator 26B. Together, these rotation angles represent a polarization-altering configuration that enforces and acts on polarization states $PS_p$ and $PS_a$, thereby impressing a sufficient amount of phase information onto radiation 14 to augment the spectroscopic data. Such additional phase information may or may not be sufficient for traditional ellipsometry, but it does support the practice of enhanced or phase-compensated sensitivity-enhance spectroscopy (PCSES) in accordance with the present invention.

Note that although the presence of supplementary compensator 26B is optional, the rotation angle $C_2$ that it introduces is easily included in the mathematical description of the method. Specifically, the combined effect on delimited phase shift Δ of the combination of rotation angles $C_1$, $C_2$ is easy to describe. Therefore, supplementary compensator 26B will be presumed present in the polarization-altering configurations discussed.

According to the method, detector 36 measures first spectrum 38A of response beam 30 when angles P, A, $C_1$, $C_2$ are in a fist polarization-altering configuration. A second spectrum 38B is measured when angles P, A, $C_1$, $C_2$ are in a second polarization-altering configuration. First and second spectra 38A, 38B thus measured are communicated to computation unit 40, which collects them and derives from them a phase-compensated and sensitivity-enhanced spectrum 44 (see FIG. 5).

Theory for Selecting Polarization-Altering Configurations

It is important to choose advantageous polarization-altering configurations when practicing phase-compensated and sensitivity-enhanced spectroscopy (PCSES). Such choices are best made after studying the impact of any given polarization-altering configuration on the s and p polarizations of radiation 14 as it propagates through apparatus 10 and is reflected from (or transmitted through) sample 28. A useful convention for such examination involves rotation matrices to describe the rotation angles of polarization-altering configurations mathematically, and Jones matrices to describe the retardance of compensators 26A, 26B and any action of polarizer 20 and analyzer 32 on radiation 14. In general, the portion of radiation 14 that reaches detector 36, called $i_{out}$, can be related to radiation 14 emitted by source 12, called $i_{in}$, by the following equation:

$$i_{out} = J_A R(A) R(-C_2) J_{C2} R(C_2) J_R R(-C_1) J_{C1} R(C_1) R(-P) J_P i_{in},$$ (Eq. 3a)

where $i_{in}$ is incident radiation 14 expressed as:

$$i_{in} = \begin{pmatrix} 1 \\ 0 \end{pmatrix},$$

and R(α) is a rotation matrix, where α=P, A, $C_1$, $C_2$ is the assumed polarization-altering configuration, such that:

$$R(\alpha) = \begin{pmatrix} \cos\alpha & \sin\alpha \\ -\sin\alpha & \cos\alpha \end{pmatrix}.$$

To understand the effect of the combination of $C_1$ and $C_2$ on Δ, it is useful to realize that R(α)R(−β)=R(α−β). $J_{C1}$ and $J_{C2}$ are the Jones matrices of compensators 26A, 26B and they are given by:

$$J_C = \begin{pmatrix} \exp(i\Delta) & 0 \\ 0 & 1 \end{pmatrix}.$$

Here, finally, the effect of delimited phase shift Δ on radiation 14 is spelled out. Thus, the selection of wavelengths of interest, e.g., $\lambda_s$, $\lambda_c$, $\lambda_l$, or partially continuous spectral ranges of interest, or even the full and continuous spectral range 16 as used in the present embodiment should be matched with the physical parameters, such as composition and thickness D of compensators 26A, 26B to achieve the necessary restrictive effect on the finely-vibrating spectrum. Specifically, thickness D is preferably thin enough so that the periodicity imposed on any spectrum that will be measured by detector 36 does not exceed its optical resolution or spectral bandwidth, SBW. On the other hand, the calculation performed by computing unit 40 can be averaged over an appropriate wavelength range for each wavelength, to include the effect from the SBW of detector 36, whenever necessary. Practically, this means that thickness D should reside between about 0.1-0.3 mm for a single plate multiple order waveplate.

Polarizer 20 and analyzer 32 simply pass radiation 14 in polarization states aligned with their polarization axes 22, 34 respectively, while blocking the orthogonal polarization states. Therefore, their Jones matrices $J_P$ and $J_A$ are:

$$J_P = J_A = \begin{pmatrix} 1 & 0 \\ 0 & 0 \end{pmatrix}.$$

Meanwhile, sample 28 has a more complex Jones matrix $J_R$:

$$J_R = \begin{pmatrix} r_{pp} & r_{ps} \\ r_{sp} & r_{ss} \end{pmatrix},$$

where the r's are the complex reflection coefficients, and the off-diagonal elements $r_{sp}=r_{ps}=0$ when sample 28 is isotropic. Subscripts p and s denote polarizations of radiation 14 as defined with reference to incidence plane IP, with p being in IP and s being orthogonal to IP, as indicated for reference purposes with dashed arrows in FIG. 4.

When the rotation matrices, Jones matrices and vector expressions for radiation 14 are plugged into equation 3a, we obtain another expression of it as follows:

$$i_{out} = \begin{pmatrix} X(\Delta_2, C_2, A) & Y(\Delta_2, C_2, A) \\ 0 & 0 \end{pmatrix} \begin{pmatrix} r_{pp} & r_{ps} \\ r_{sp} & r_{ss} \end{pmatrix} \begin{pmatrix} X(\Delta_1, C_1, P) \\ Y(\Delta_1, C_1, P) \end{pmatrix}.$$ (Eq. 3b)

In this expression $X(\Delta,C,V)$ and $Y(\Delta,C,V)$, where $V=A$ or $P$, are defined as:

$$X(\Delta,C,V) = \exp(i\Delta)\cos C \cos(V-C) - \sin C \sin(V-C) \quad \text{(Eq. 3c)}$$

$$Y(\Delta,C,V) = \exp(i\Delta)\sin C \cos(V-C) + \cos C \sin(V-C) \quad \text{(Eq. 3d)}$$

Therefore, the end-to-end transmittance T of apparatus 10 can be expressed by:

$$T = |X_1 X_2 r_{pp} + Y_1 Y_2 r_{ss} + X_1 Y_2 r_{sp} + X_2 Y_1 r_{ps}|^2, \quad \text{(Eq. 4)}$$

with $X_1 = X(\Delta_1, C_1, P)$, $X_2 = X(\Delta_2, C_2, A)$, $Y_1 = Y(\Delta_1, C_1, P)$, $Y_2 = Y(\Delta_2, C_2, A)$. Clearly, multiple polarization-altering configurations set by rotation angles P, A, $C_1$ and $C_2$ can be used to measure multiple spectra 38 of sample 28, besides first and second spectra 38A, 38B.

Advantageous choices of polarization-altering configurations will now be described by initially concentrating on a simple case. In this case $r_{sp} = r_{ps} = 0$ (isotropic sample 28) and $\Delta_2 = 0$ (or equivalently, $C_2 = A$), $X_2 = \cos A$ and $Y_2 = \sin A$. Note that this is similar to the set-up of the familiar polarizer-compensator-sample-analyzer (PCSA) ellipsometer. Because of these simplifications, we can set $\Delta = \Delta_1$ and $C = C_1$. Now the end-to-end transmittance T reduces to:

$$T = |a_s + a_p|^2, \quad \text{(Eq. 5)}$$

where:

$$a_p = r_p \cos A [\exp(i\Delta)\cos C \cos(P-C) - \sin C \sin(P-C)], \quad \text{(Eq. 6)}$$

$$a_s = r_s \sin A [\exp(i\Delta)\sin C \cos(P-C) + \cos C \sin(P-C)]. \quad \text{(Eq. 7)}$$

Here $r_s = r_{ss}$ and $r_p = r_{pp}$ are the complex reflection coefficients of sample 28 for s-polarized and p-polarized incident radiation 14, as defined with reference to incidence plane IP.

When $C = C_1 = 0°$ we obtain the following equation for end-to-end transmittance T:

$$T = R_p \cos^2 A \cos^2 P + R_s \sin^2 A \sin^2 P + \tfrac{1}{2}\sqrt{R_p R_s}\sin(2A)\sin(2P)\cos(\Delta+\delta). \quad \text{(Eq. 8a)}$$

Then, for $C = C_1 = 90°$ we obtain an end-to-end transmittance T:

$$T = R_p \cos^2 A \cos^2 P + R_s \sin^2 A \sin^2 P + \tfrac{1}{2}\sqrt{R_p R_s}\sin(2A)\sin(2P)\cos(\Delta-\delta). \quad \text{(Eq. 9a)}$$

In these equations $\delta$ is the phase difference between $r_p$ and $r_s$, and $R_s = |r_s|^2$, $R_p = |r_p|^2$. When rotation angles of polarizer 20 and analyzer 32 are both 45° the first polarization-altering configuration is $P = 45°$, $A = 45°$, $C = 0°$ and the second one is $P = 45°$, $A = 45°$, $C = 90°$. This produces end-to-end transmittances:

$$T = \tfrac{1}{4}[R_s + R_p + 2\sqrt{R_s R_p}\cos(\Delta+\delta)], \quad \text{(Eq. 8b)}$$

$$T = \tfrac{1}{4}[R_s + R_p + 2\sqrt{R_s R_p}\cos(\Delta-\delta)]. \quad \text{(Eq. 9b)}$$

For another pair of polarization-altering configurations described by $P = 45°$, $A = -45°$, $C = 0°$ and $P = 45°$, $A = -45°$, $C = 90°$ we obtain:

$$T = \tfrac{1}{4}[R_s + R_p - 2\sqrt{R_s R_p}\cos(\Delta+\delta)], \quad \text{(Eq. 8c)}$$

$$T = \tfrac{1}{4}[R_s + R_p - 2\sqrt{R_s R_p}\cos(\Delta-\delta)]. \quad \text{(Eq. 9d)}$$

The above equations indicate how advantageous polarization-altering configurations can be derived from the most general formulation of end-to-end transmittance T. Apparatus 10 of FIG. 3 can now be employed for optical characterization of sample 28 in accordance with the phase-compensated sensitivity-enhanced spectroscopy (PCSES) method of the invention. The characterization relies on relating measurements of changes in measured quantity T to changes in underlying parameters of sample 28, notably $R_s$, $R_p$ and $\delta$. For this reason, it is preferable for the sensitivity of T with respect to variation in $R_s$, $R_p$, and/or $\delta$ to be maximized. More specifically, there are often situations in practice where $\Delta$ depends more sensitively on properties of sample 28 than $R_s$ or $R_p$, so the sensitivity of T with respect to changes in $\delta$ is of particular interest. From equations 8 and 9, it can be seen that the factor $\sin(2P)\sin(2A)$ in $\delta$-dependent terms of equations 8a and 9a has a maximum magnitude when P and A are both odd integer multiples of 45°. Accordingly, these are the preferred rotation angles for polarizer 20 and analyzer 32 to be used in polarization-altering configurations.

In equation 8, the effect of compensator 26A is to change the $\delta$-dependent term of T from a term proportional to $\cos\delta$ to a term proportional to $\cos(\Delta+\delta)$. Surprisingly, it has been found that this apparently modest change can provide substantial improvements in characterization performance, especially in connection with thin film characterization. The benefits are most apparent in situations where $\delta$ of sample 28 is close to 0° or 180°. This is often the case in practice, especially for thin films on a Si substrate. The sensitivity of a term proportional to $\cos\delta$ to variations in $\delta$ is small for $\delta$ near 0° or 180°, because $\sin\delta$ (i.e., $d\cos\delta/d\delta$) is close to zero under these assumptions. In contrast, the sensitivity of a term proportional to $\cos(\Delta+\delta)$ to variations in $\delta$ is not necessarily small for $\delta$ near 0° or 180°, because $\sin(\Delta+\delta)$ need not be close to zero under these assumptions.

Given these theoretical underpinnings the ideas of embodiments of the invention can now be fully appreciated. In particular, phase compensation as provided by $\Delta$ is one element, fine-vibrations due to $\Delta$-dependence in equations 8 and 9 is another element, and performing measurements at multiple wavelengths is still another element of the present method. Accordingly, it is convenient to regard the various embodiments of the invention as relating in general terms to a novel technique, herein referred to as phase-compensated sensitivity-enhanced spectroscopy (PCSES).

Considerations for Useful Polarization-Altering Configurations

The basic polarization-altering configurations and issues in irradiating sample 28 by radiation 14 are thus outlined. It is now time to review several specific details that will further aid in the implementation of phase-compensated sensitivity-enhanced spectroscopy (PCSES). In particular, there are a few more fundamental considerations affecting polarization-altering configurations. When $C = 0°$ or 90°, the fast axes of compensator 26A are aligned with the p- or s-polarization directions defined with respect to incidence plane IP. In this situation, there is a substantial simplification based on the fact that birefringent elements having aligned principal axes commute when the sample is isotropic. In other words, it does not matter which element is encountered first by radiation 14 passing through apparatus 10. Sample 28, compensator 26A, and, when used, supplementary compensator 26B are the birefringent elements. Note that it is possible to practice the invention with supplementary compensator 26B only, in which case the birefringent elements are sample 28 and compensator 26B.

Clearly, equations 8 and 9 cover cases where both compensator 26A and supplementary compensator 26B are present. In these embodiments one can assign delimited phase shift $\Delta_1$ to compensator 26A and delimited phase shift $\Delta_2$ to supplementary compensator 26B. Then the total or effective phase shift $\Delta$ in equations 8 and 9 can be set to any of the quantities $\Delta_1+\Delta_2$, $\Delta_1-\Delta_2$, $-\Delta_1+\Delta_2$, $-\Delta_1-\Delta_2$ by setting rotation angles $C_1$ and $C_2$ to 0° or 90°. Also, effective phase shift $\Delta$ in equations 8 and 9 can be set to $\Delta_1$ or $-\Delta_1$ by setting rotation angles $C_1$ to 0° or 90° and $C_2=A$. Furthermore, $\Delta$ in equations 6 and 7 can be set to $\Delta_2$ or $-\Delta_2$ by setting $C_2$ to 0° or 90° and $C_1=P$. A person skilled in the art will appreciate that all these simplifying choices offer considerable flexibility in the practice of phase-compensated sensitivity-enhanced spectroscopy (PC-SES) and can also be derived from the general equations 3 and 4. In fact, despite the multiplicity of possible choices, usually the most useful values for setting rotation angles P, A, $C_1$ and $C_2$ for the first and second polarization-altering configurations as well as any other polarization-altering configurations include 0°, 45°, 90°, −45° and integer multiples thereof.

Often, a calibration of delimited phase shift $\Delta$ in a particular apparatus 10 using specific compensators 26A and/or 26B is required prior to commencing a series of phase-compensated spectroscopic measurements. This can be done by measuring a baseline or first spectrum 38A with first polarization-altering configuration being: P=A=C=90°. Then, a calibration measurement or second spectrum 38B can be taken with second polarization-altering configuration being: P=A=90°, C=45°. The ratio of second spectrum 38B to first spectrum 38A in this situation is (1+cos A)/2, from which the value of $\Delta$, or $(n_e-n_o)$, as a function of wavelength $\lambda$ and thickness D, can be obtained and employed in equation 1.

General Practice of PCSES

Figure 5:
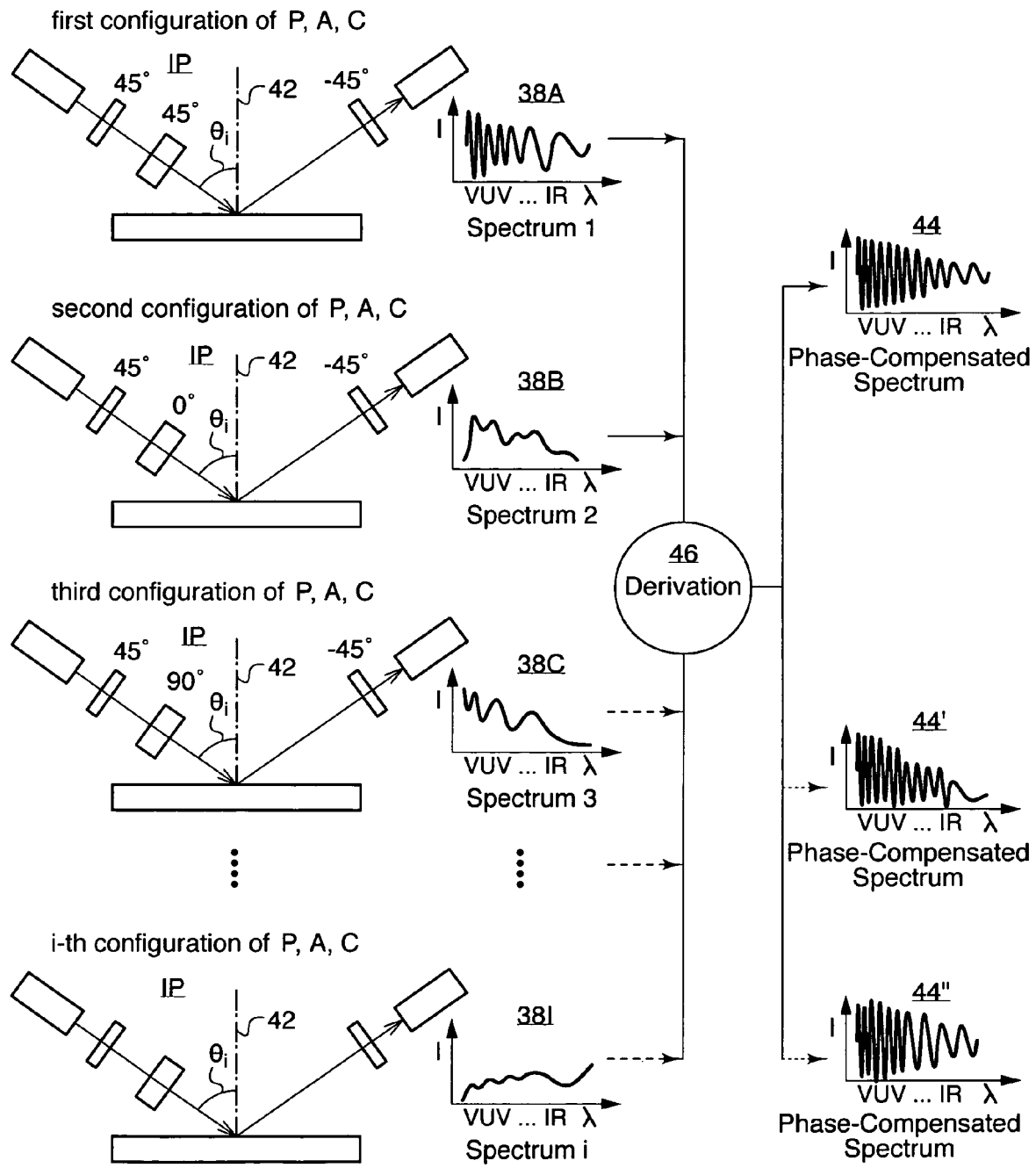
FIG. 5 is a diagram that shows how spectra obtained under different polarization-altering configurations are used to derive a phase-compensated spectrum according to the invention.

Having reviewed the theoretical fundamentals, simplifications applicable to practical polarization-altering configurations as well as important calibration issues, we will now refer to FIG. 5 to present the most general way of practicing phase-compensated sensitivity-enhanced spectroscopy (PCSES). FIG. 5 illustrates how a series of spectra 38A, 38B, 38C, . . . 38I are collected at distinct polarization-altering configurations defined by rotation angles P, A and C. Here C stands for a combination of compensators 26A, 26B at rotation angles $C_1$ and $C_2$ or just compensator 26A set at rotation angle C. Simplified apparatus 10 along a cross-sectional view taken in incidence plane IP and indicating the polarization-altering configurations is shown alongside each of spectra 38 for better understanding.

It should be noted upfront, that by collecting a sufficient number of spectra 38 the full Jones matrix $J_R$ of sample 28 could be determined. This would allow one to then obtain the normalized full Stokes vector. Now, although apparatus 10 can be employed to obtain complete polarization data and to practice ellipsometry, the PCSES method of the invention requires substantially less data and is thereby novel in its approach. Typically, ellipsometry would require at least four spectra 38, while the present method can be practiced with just two, namely spectra 38A, 38B, as long as an advantageous choice of polarization-altering configurations is made in accordance with the teachings of the invention.

Specifically, first spectrum 38A is collected at first polarization-altering configuration P=45°, A=−45°, C=45° and second spectrum 38B is collected at second polarization-altering configuration P=45°, A=−45°, C=0°. Spectra 38A, 38B are communicated to computation unit 40 which performs a derivation step 46 to obtain phase-compensated spectrum 44 from them. Derivation step 46 may involve any operation, ranging from examining spectra 38A, 38B side-by-side to combining them in accordance with any combinatorial procedure. For example, derivation step 46 can convolve, sum, subtract or form a ratio of spectra 38A, 38B. In the present case, step 46 derives phase-compensated spectrum 44 from a ratio of spectra 38A, 38B. Phase-compensated spectrum 44 is then used for characterization of sample 28. This may include determination of optical parameters n, k, and derivation of thickness t of any thin film 48 residing on the surface of sample 28 (indicated in dashed lines in FIG. 4). Of course, other physical parameters can also be determined, e.g., critical dimensions such as trench width or depth in cases where sample 28 carries a grating or other structure on its surface.

Although two spectra 38A, 38B collected at different polarization-altering configurations are sufficient to implement phase-compensated spectroscopy and characterize sample 28, or thin film 48 in particular, additional spectra 38 can be taken. As shown in FIG. 5, a third spectrum 38C is collected at a third polarization-altering configuration P=45°, A=−45°, C=90° and submitted to computation unit 40 along with spectra 38A, 38B for derivation of phase-compensated spectrum 44'. It is worth remarking, that three spectra 38A, 38B, 38C are typically still insufficient to practice ellipsometric characterization.

At least one more supplementary spectrum can be collected when polarization states $PS_p$, $PS_a$ of radiation 14 and compensator 26A are in at least one corresponding polarization-altering configuration as defined by angles P, A, C. FIG. 5 illustrates a series of such supplementary spectra 38 ranging up to i-th spectrum 38I collected under an i-th polarization-altering configuration. A phase-compensated spectrum 44" is then derived by computation unit 40 in step 46 from first through i-th supplementary spectra 38A-38I. It should be noted, that with just one supplementary spectrum, i.e., with four spectra 38 or i=4, it is possible to derive a full-fledged ellipsometric measurement of sample 28. That is because four spectra provide sufficient information to solve the polarization-based equations describing sample 28, e.g., the Stokes vector or other equivalent mathematical formulations.

Besides the specific polarization-altering configurations chosen above, there are other easy to implement embodiments. Recall that polarization-altering configurations are set by the type of alignment of polarization states $PS_p$, $PS_a$ and of principal axis PA1 of compensator 26A, and optionally of principal axis PA2 of supplementary compensator 26B. In the convention chosen here, principal axis PA1 corresponds to the "fast axis" or extraordinary axis associated with refractive index $n_e$. Now, in one simple embodiment, first polarization-altering configuration is achieved by aligning polarization states $PS_p$, $PS_a$ via alignment of P and A (i.e., P=A=0°) and principal axis PA1 of compensator 26A at 0°. The second polarization-altering configuration is obtained through non-alignment of polarization states $PS_p$, $PS_a$ (i.e., P=A=0°) and principal axis PA1 of compensator 26A is not at 0° but at 45°. In other words, in this example the convenient non-alignment is accomplished by rotating principal axis PA1 of compensator 26A by 45° with respect to the first polarization-altering configuration. Meanwhile, polarization states $PS_p$, $PS_a$ remain aligned (P=A).

A person skilled in the art will recognize that the above teaching provides all the necessary tools to devise many advantageous choices of first, second, and, if necessary, third and supplementary polarization-altering configurations. These choices will be based on the specifics of apparatus 10 as well as the nature of sample 28 and any system parameters that may be known in advance. Therefore, apparatus 10, and the polarization-altering configurations given so far, as well as exemplary spectra 16, 38, 44 shown in FIGS. 3, 4 and 5 should be treated as instructive of the principles behind the novel PCSES method, without in any way limiting the scope of applicability of the method. To further help those skilled in the art in making advantageous choices of elements in apparatus 10 as well as correspondingly advantageous polarization-altering configurations, we will now review some practical examples and resulting measurements.

Practical Examples and Preferred Embodiments

In one particularly preferred embodiment, same-sample calibration is performed with first polarization-altering configuration set at: P=−A=C=45°. Then a measurement is made with second phase-altering configuration set at: P=−A=45°, C=0°. This choice is advantageous because first and second spectra 38A, 38B are mathematically simple expressions, namely $R_s+R_p-2\sqrt{R_s R_p}\cos\delta$ and $R_s+R_p-2\sqrt{R_s R_p}\cos(\Delta+\delta)$, respectively. As previously defined, δ is the phase difference between $r_p$ and $r_s$, $R_s=|r_s|^2$, $R_p=|r_p|^2$ and delimited phase shift Δ due to the combination of angles $C_1$ and $C_2$. Several choices of rotation angles $C_1$ and $C_2$ may yield similar effective Δ as explained above.

The phase-compensated spectrum expressed in terms of end-to-end transmittance T derived by computation unit 40 from first and second spectra 38A, 38B in this preferred embodiment is a ratio defined as:

$$T = \frac{R_s + R_p - 2\sqrt{R_s R_p}\cos(\Delta+\delta)}{R_s + R_p - 2\sqrt{R_s R_p}\cos\delta}. \qquad \text{(Eq. 10)}$$

In this preferred embodiment, P, A and C need not be exactly at the nominal values when measuring second spectrum 38B. In fact, if the deviation from the nominal values are small enough (i.e., <10°), sufficiently accurate results can be obtained, as long as the actual values of P, A and C are used with equation 4 by calculation unit 40 in deriving phase-compensated spectrum 44.

Figure 6:
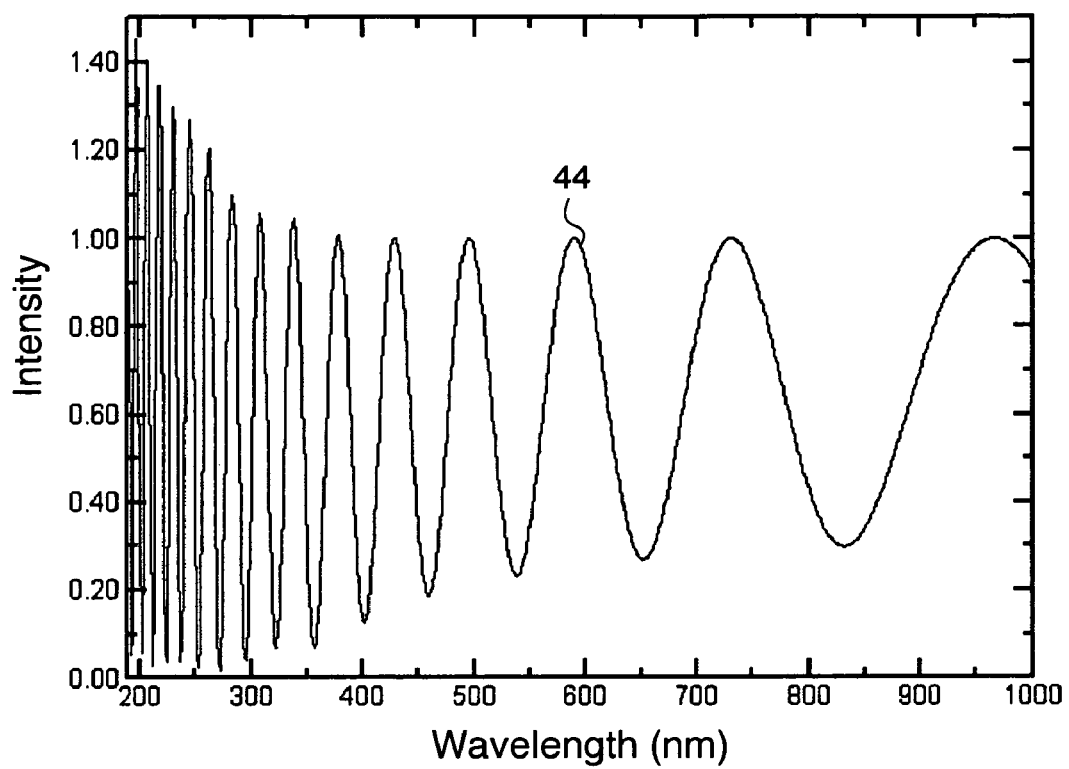
FIGS. 6-9 are phase-compensated spectroscopy graphs as computed for several phase-altering configurations and under differing circumstances.

FIG. 6 is a graph showing the results of applying equation 10 to a sample 28 made of a Si substrate carrying a 2 nm $SiO_2$ layer on its top surface. Beam 18 has an angle of incidence $\theta_i=65°$. Only compensator 26A is used and it consists of a $MgF_2$ wave plate of thickness D=0.25 mm. The periodic behavior or finely-vibrating spectrum of the graph of phase-compensated sensitivity-enhanced spectrum 44 (PCSES spectrum) is due to the dependence of retardance expressed by delimited phase shift Δ on wavelength λ. To first order, Δ for a wave plate varies as 1/λ, and the dispersion of $n_o$ and $n_e$ also contributes to the dispersion of Δ (see equations 1 & 2). In this example, it is preferred for P=−A=45° as opposed to P=A=45°, which would also work. The reason for the preference is that cos δ is <0 for a bare Si wafer, and is also <0 for a thin film 48 on top of Si. This preferred choice of signs avoids undesirable cancellation in the denominator of equation 10 that would decrease measurement signal to noise ratio (SNR).

Another embodiment employs reference-sample calibration. In this approach, a calibration is performed on a known sample or reference-sample at polarization-altering configuration P=−A=C=45°. By comparing the end-to-end transmittance for the calibration measurement, $T_0^{exp}(\lambda)$, to calculated results for the known sample, $T_0^{cal}(\lambda)$, the system baseline transmission $T_0(\lambda)=T_0^{exp}(\lambda)/T_0^{cal}(\lambda)$ can be obtained. Then, measurements on an unknown sample can be performed with polarization-altering configuration P=−A=45°, C=0°. These measured results can be provided as an output by dividing by baseline transmission $T_0(\lambda)$, which corrects for wavelength dependent system attenuation, wavelength dependent detector efficiency, etc. The intent of this calibration is to provide experimental measurements that correspond closely to equations 8 and 9.

Figure 7:
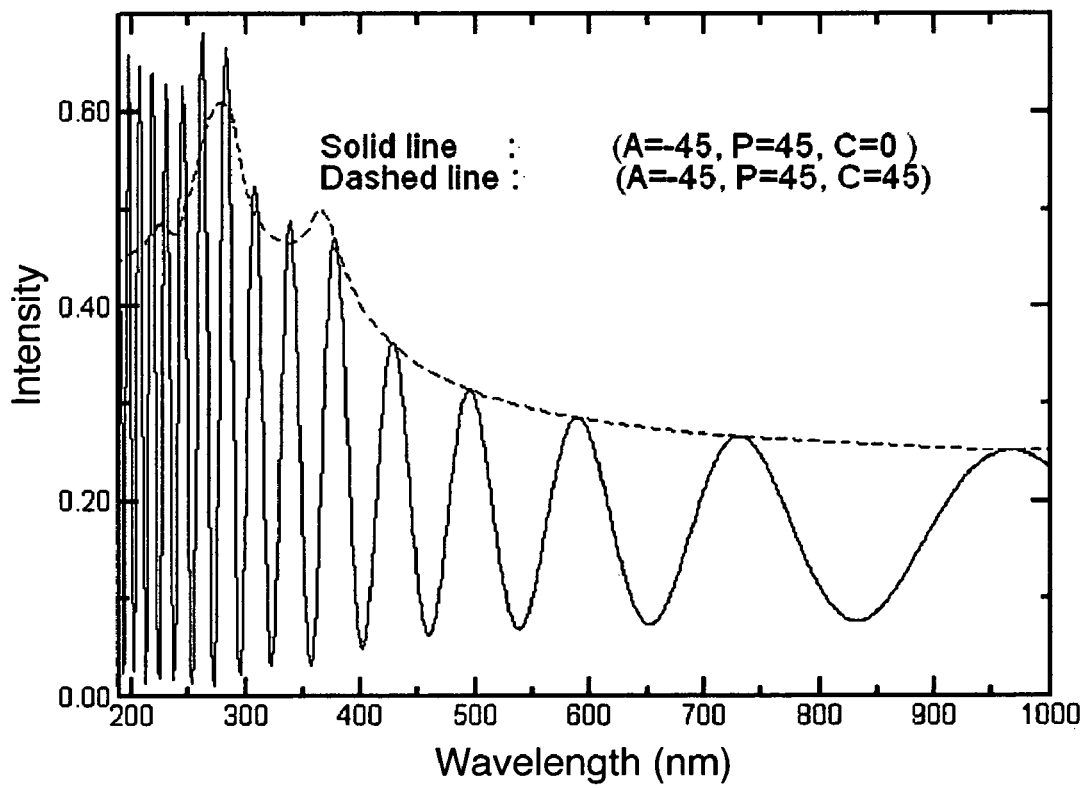

FIG. 7 shows exemplary results that can be obtained in this embodiment. The solid line shows the results of equation 8 as applied to the example of FIG. 6, with P=−A=45°, and C=0°. The dashed line in FIG. 7 shows the results when P=−A=C=45°. Same-sample calibration, as in the embodiment graphed in FIG. 6, can be obtained by taking a ratio of the solid line to the dotted line in FIG. 7. In this case, the effect of the reference-sample calibration has been divided out.

Figure 8:
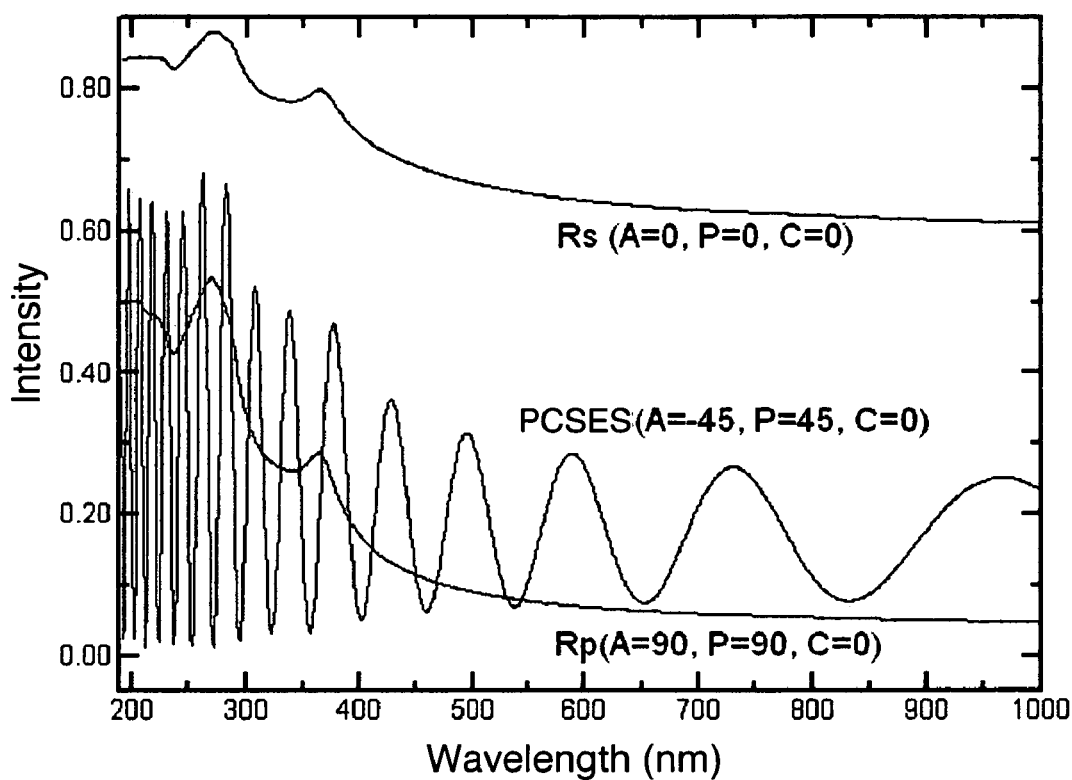

As an extension of the reference-sample calibration approach, $R_s$ and $R_p$ results can also be provided. FIG. 8 shows calculated results for the example of FIGS. 6 and 7. $R_s$ can be measured by setting P=A=C=0°. $R_p$ can be measured by setting P=A=90°, C=0°. The phase-compensated sensitivity-enhanced spectrum or the PCSES spectrum is also shown. This demonstrates one of the advantages provided by apparatus 10 of the invention: both reflectometry spectra and ellipsometry-like spectra can be provided by same apparatus 10.

It can be helpful to calibrate for each pertinent orientation of polarizer 20 and analyzer 32, because the system baseline may depend on orientation of polarizer 20 and/or analyzer 32. For example, same-sample $R_s$ calibration can be performed as follows. First, it is assumed that the optical intensity passed through polarizer 20 is 1 for P=0°, $I_{45}$ for P=45°, and $I_{-45}$ for P=−45°. Next, it is assumed that the efficiency of detector 36 is 1 for A=0°, $S_{45}$ for A=45°, and $S_{-45}$ for A=−45°.

Let M(P,C,A) be the measured system transmittance as a function of angles P, C, and A. Under these assumptions we have:

$$M(0,0,0)=R_s;$$

$$M(45,0,0)=I_{45}R_s/2;$$

$$M(-45,0,0)=I_{-45}R_s/2;$$

$$M(0,0,45)=S_{45}R_s/2;$$

$$M(0,0,-45)=S_{-45}R_s/2. \qquad \text{(Eq. 11)}$$

From these equations, the sample-independent calibration parameters $I_{45}$, $I_{-45}$, $S_{45}$ and $S_{-45}$ can be determined at each wavelength λ of interest. With these calibration parameters available, the following normalized measurements can be made:

$$\frac{M(-45,0,45)}{R_s I_{-45} S_{45}} = (1/4)[1+R_p/R_s - 2\sqrt{R_p/R_s}\cos(\Delta+\delta)]; \qquad \text{(Eq. 12a)}$$

$$\frac{M(-45,45,45)}{R_s I_{-45} S_{45}} = (1/4)[1+R_p/R_s - 2\sqrt{R_p/R_s}\cos(\delta)]; \qquad \text{(Eq. 12b)}$$

$$\frac{M(45,0,45)}{R_s I_{45} S_{45}} = (1/4)[1+R_p/R_s + 2\sqrt{R_p/R_s}\cos(\Delta+\delta)]; \qquad \text{(Eq. 12c)}$$

$$\frac{M(45,45,45)}{R_s I_{45} S_{45}} = (1/4)[1+R_p/R_s + 2\sqrt{R_p/R_s}\cos(\delta)]. \qquad \text{(Eq. 12d)}$$

Figure 9:
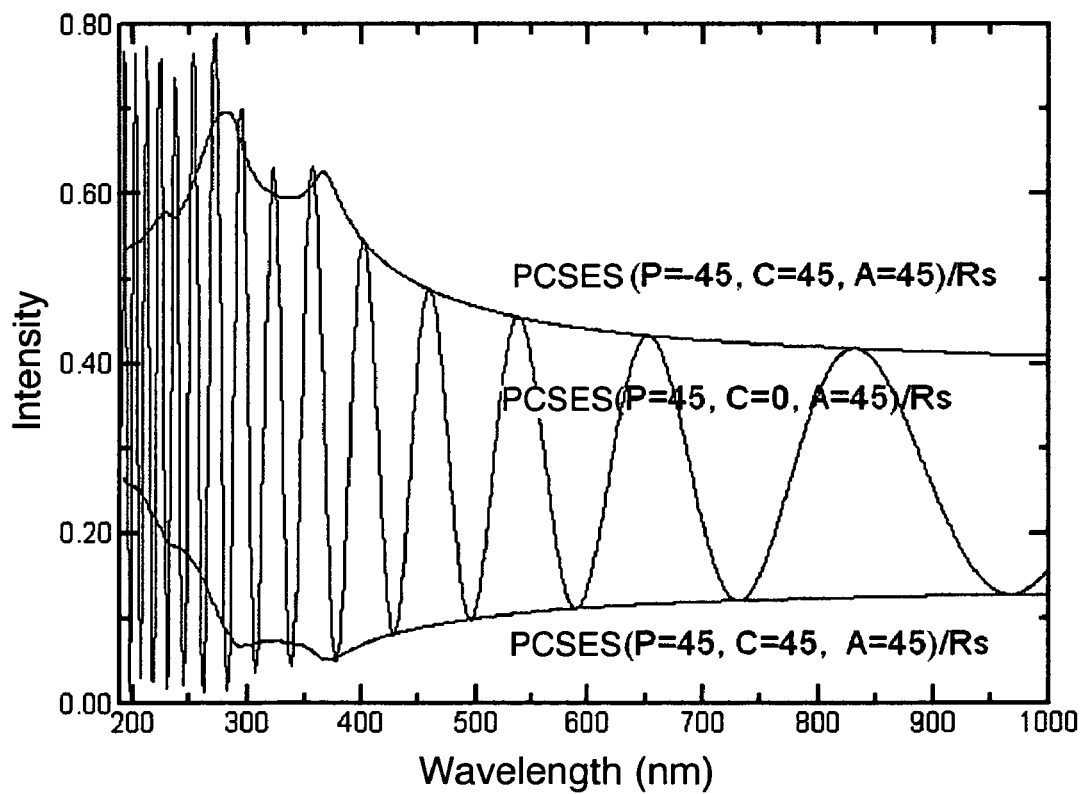

FIG. 9 shows graphs of equations 12b-d for $\theta_i=65°$ on sample 28 consisting of a Si substrate with a 2 nm $SiO_2$ layer on top of its surface. In this case compensator 26A is made of MgF$_2$ and has a thickness D=0.25 mm.

The results of equations 12a-d can also be employed to determine ellipsometric parameters of sample 28. The traditional ellipsometry parameters δ and ψ are defined by $r_p/r_s = \tan(\psi)\exp(i\delta)$. Here the definition of the parameter δ provided above in equations 8 and 9 is consistent with δ as defined by ellipsometry. First, adding equation 12a to 12c (or equation 12b to 12d) provides a measured quantity from which $R_p/R_s$ can be readily obtained. The ψ parameter follows from $\tan(\psi) = \sqrt{R_p/R_s}$. Second, subtracting equation 12b from 12d provides a measured quantity from which cos(δ) can be determined (since $R_p/R_s$ is known at this point in the calculation). Third, sin(δ) can be extracted from equation 12a and/or 12c, to remove the ambiguity in going from cos(δ) to δ, since $R_p/R_s$ and cos(δ) are determined from the first two steps.

The following additional quantity can be measured:

$$\frac{M(-45, 90, 45)}{R_s I_{-45} S_{45}} = (1/4)[1 + R_p/R_s - 2\sqrt{R_p/R_s}\cos(\Delta - \delta)]. \quad (\text{Eq. 12e})$$

This corresponds to the polarization-altering configuration expressed in equation 12a, except that compensator's 26A angle $C_1$ is 90° instead of 0°. We now have:

$$\frac{M(-45, 90, 45)}{R_s I_{-45} S_{45}} + \frac{M(-45, 0, 45)}{R_s I_{-45} S_{45}} = \sec^2(\psi/2) - \tan\psi\cos\Delta\cos\delta \quad (\text{Eq. 13})$$

$$\frac{M(-45, 90, 45)}{R_s I_{-45} S_{45}} + \frac{M(-45, 0, 45)}{R_s I_{-45} S_{45}} = \tan\psi\sin\Delta\sin\delta.$$

Here it is apparent that δ can be uniquely determined from cos δ and sin δ, since Δ can be found by calibration, as described above. In general, the more phase-compensated spectra 44 are used, i.e., an entire series as shown in FIG. 5, the better the SNR will be in the analysis performed by computation unit 40. Meanwhile, in order to avoid "dead spots" (i.e., ranges where cos Δ≈0 and/or sin Δ≈0) in the sensitivity of equation 13 to changes in δ, the above-described ability to use multiple compensators 26 to adjust the net Δ of the system is helpful.

Typically, a dispersion model is needed when the complex refraction coefficients n, k and thickness t of thin film 48 are determined simultaneously. The number of variables in the process of extracting thickness t and n, k spectra for thin film 48 and/or other thin films or structures (not shown) that may be sandwiched in sample 28 from phase-compensated spectra 44 is greatly affected by the dispersion model. The difficulty of this procedure can be vastly reduced by the proper choice of a valid and advantageous model, such as the Forouhi-Bloomer dispersion equations taught by U.S. Pat. No. 4,905,170.

Figure 10A:
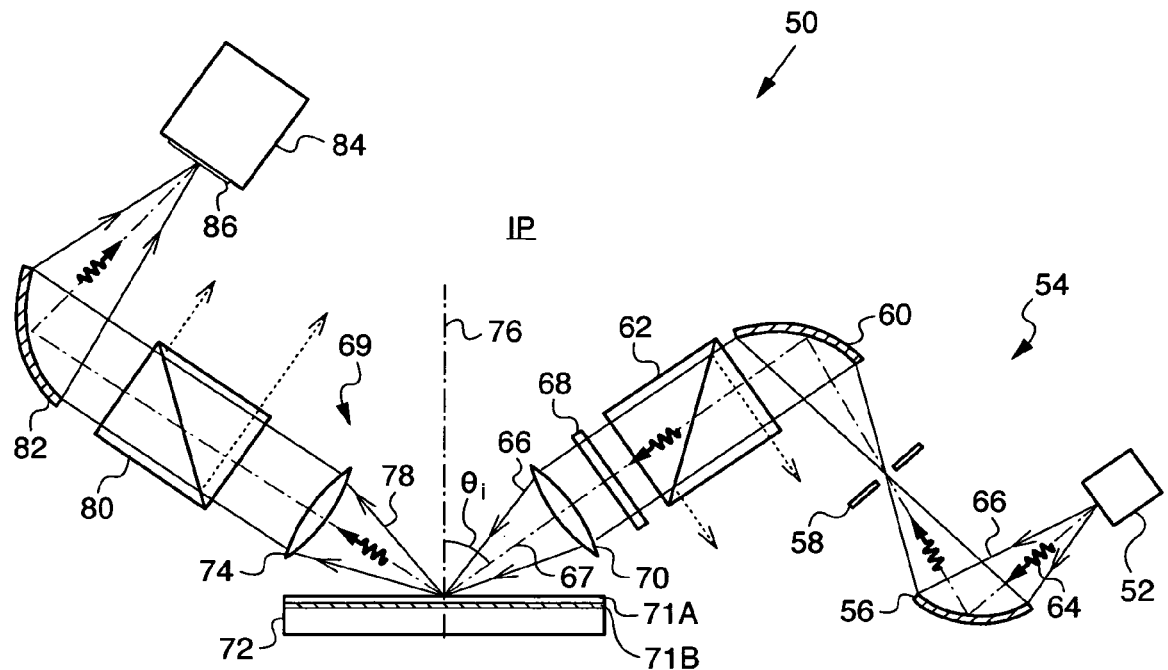
FIG. 10a is a side view of another apparatus for phase-compensated spectroscopy according to the invention.

FIG. 10a is a plan side view of a preferred apparatus 50 for practicing PCSES. Apparatus 50 has a source 52 and a collimator 54 including a first mirror 56, an aperture 58, a second mirror 60 and a polarizer 62. Preferably, first mirror 56 is a toroidal mirror and second mirror 60 is a parabolic mirror. Toroidal mirror 56 is preferred because it can efficiently focus a beam 66 of radiation 64 from source 52 to a small spot at the plane of aperture 58. In fact, toroidal mirrors are especially suitable for spot to spot focusing. Having second mirror 60 be parabolic is preferred in order to accurately collimate beam 66 of radiation 64 passing through aperture 58. This specific configuration of mirrors 56, 60 has the advantage of providing, with just a two-mirror system, collimated beam 66 having low aberration and having aperture 58 to control spot size. If spherical mirrors were employed to provide these functions, the complexity of apparatus 50 would increase (i.e., more mirrors) and/or aberration would increase.

This source assembly provides collimated beam 66 of radiation 64 in a state of polarization PS$_p$, as required to practice the method of invention. Note that polarizer 62 is of the variety that deflects radiation 64 in orthogonal polarization state PS$_s$, as shown by dashed arrows, rather than absorbing it. It is further preferable for source 52 to be broadband, and for detector 84 to be wavelength selective, in order to facilitate spectral measurements at two or more distinct wavelengths $\lambda_1, \lambda_2, \lambda_3, \ldots \lambda_k$.

The next optical element in apparatus 50 is a compensator 68, followed by an imaging system 69 including lenses 70 and 74 for focusing beam 66 on a sample 72. Depending on the polarization-altering configuration, the polarization state of radiation 64 incident on sample 72 may or may not be PS$_p$. Note that the side view of FIG. 10a is in incidence plane IP, and thus angle of incidence $\theta_i$ of beam 66 is defined with respect to beam axis 67 in the plane of the paper with respect to surface normal 76.

Imaging system 69 forms an image of aperture 58 on sample 72. Sample 72, and more precisely, one or more layers and/or structures 71A, 71B residing on a substrate 73 that taken together comprise sample 72, generate a response beam 78. Imaging system 69 collimates response beam 78 of radiation 64 from sample 72 and passes it on to an analyzer 80. Analyzer 80 is of the type that passes a polarization state PS$_a$ and deflects, as indicated by the dashed arrows, the orthogonal polarization state. A mirror 82 that is preferably parabolic, brings response beam 78 of radiation 64 to a focus at detector 84. As in the previously discussed embodiment, polarizer 62, analyzer 80 and compensator 68 allow the user to set the desired polarization-altering configuration for measuring a particular phase-compensated spectrum.

The phase-compensated spectrum in this embodiment may consist of a number of discrete wavelengths, i.e., a subset of wavelengths $\lambda_1, \lambda_2, \lambda_3, \ldots \lambda_k$ provided by source 52, since some wavelengths may be completely blocked at certain polarization-altering configurations. In other words, the subset will depend on the selection of polarization-altering configurations and the value of delimited phase shift Δ. Clearly, detector 84 could be a multi-channel device set to wavelengths $\lambda_1, \lambda_2, \lambda_3, \ldots \lambda_k$ in this embodiment. Of course, a continuous detector, such as a spectrometer can also be used. In fact, a spectrometer is required when source 52 emits radiation 64 in a continuous spectral range rather than at discrete wavelengths $\lambda_1, \lambda_2, \lambda_3, \ldots \lambda_k$.

Lenses 70, 74 preferably have a numerical aperture (NA) of 0.3 or less, as long as the desired spot size and intensity of radiation 64 on sample 72 are achieved, since the phase-compensated spectrum signal is dependent on $\theta_i$. As NA increases, the spread of angles of incidence of separate rays on sample 72 increases and complicates the analysis, as remarked above. In practice, an angular average is often helpful for calculating phase-compensated spectra in order to better simulate the experimental spectra and improve characterization accuracy for thin films 71A, 71B.

Imaging system 69 forms a small spot on sample 72 (as opposed to an unfocused beam). This is preferred, since it is often desirable for characterization to have the lateral resolution provided by illumination with a small spot. However, imaging system 69 is not required in cases where lateral resolution is unnecessary. In cases where imaging system 69 is included, practice of the invention does not depend on details of the imaging optics. For example, reflective optics could be employed in place of one or both lenses 70, 74.

Figure 10B:
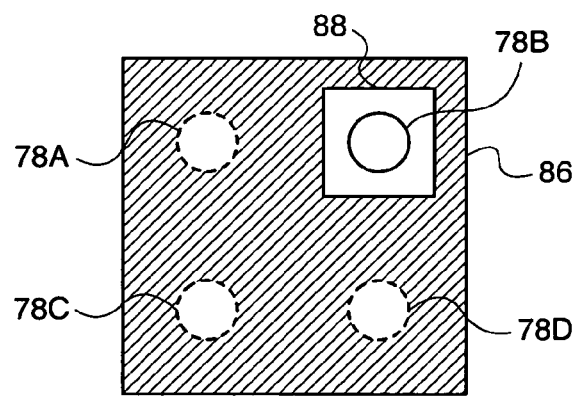

One of the motivations for this preferred embodiment is to minimize system aberration and to provide a clean separation of the polarizations to be blocked and passed. These considerations will be appreciated by reviewing FIG. 10b, which schematically shows a typical situation at detector 84. A screen 86 (also indicated in FIG. 10a) with an aperture 88 defines the input to detector 84. Radiation 64 must pass through aperture 88 to be received by detector 84.

In practice, it is important to realize that polarizer 62 and analyzer 80, e.g., each a $MgF_2$ Rochon polarizer, often do not block passage of the undesired state of polarization at polarizer 62 or analyzer 80. Instead, a lateral offset is induced between radiation 64 having the two possible polarization states. Since there are two possibilities at polarizer 62, and two possibilities at analyzer 80, there are four possible positions of incidence of response beam 78 on screen 86; namely 78A, 78B, 78C and 78D. Aperture 88 is aligned with the one of these that does not move as polarizer 62 and analyzer 80 rotate into the various polarization-altering configurations; here 78B.

However, it is important that beam positions 78A, 78B, 78C and 78D be sufficiently well separated that alignment of aperture 88 to substantially only a single beam position be possible.

If this condition is not satisfied, error will be introduced because radiation 64 having the wrong polarization state will enter detector 84. Several aspects of the previously described embodiment are intended to address this potential issue. Aperture 58 helps define the boundaries of beam positions or spots 78A, 78B, 78C and 78D on screen 86. In fact, it is preferred for apparatus 50 to include an output imaging system that forms an image of aperture 58 at the entrance plane of detector 84, i.e., on screen 86. Here, parabolic mirror 82 is included in this output imaging system. The above-described low-aberration mirror configuration is important because aberration causes blurring of spots 78A, 78B, 78C and 78D at the input plane of detector 84.

Figure 11:
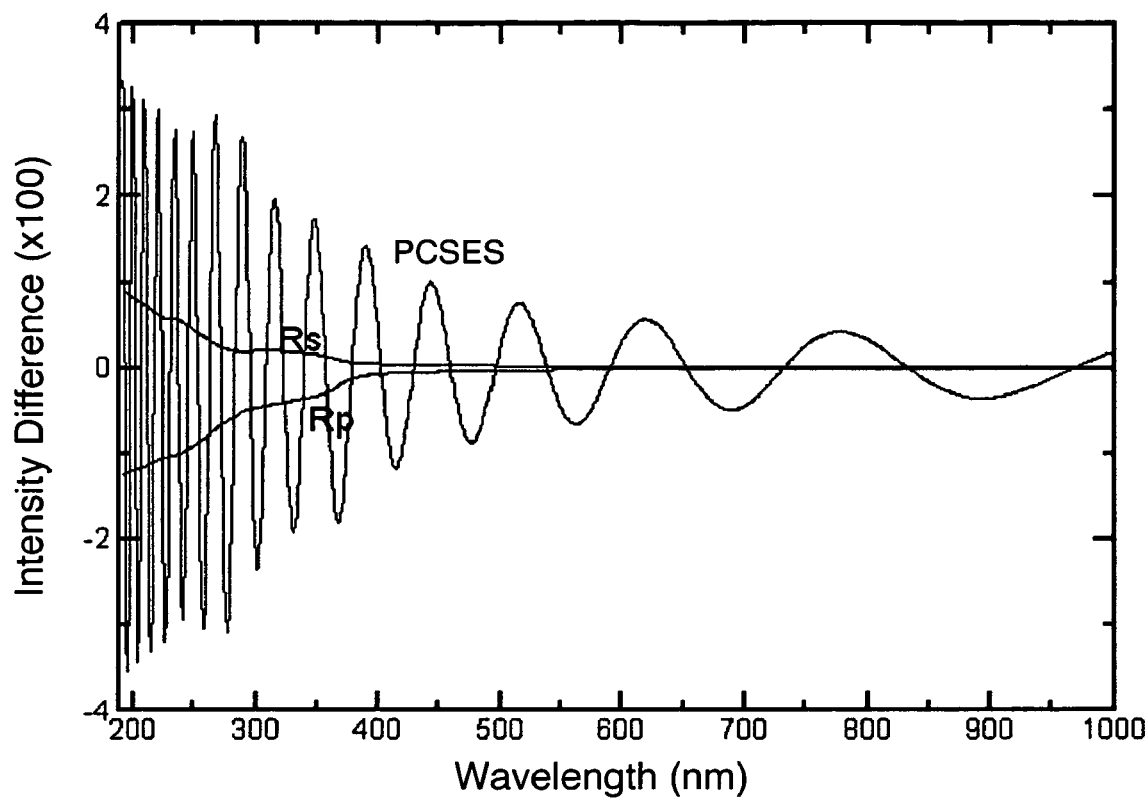
FIG. 11 is a graph showing simulation results that demonstrate enhanced characterization sensitivity provided by the invention.

FIG. 11 shows simulation results that demonstrate sensitivity-enhanced characterization sensitivity provided by the invention. In this example, two samples are considered. Sample A is made of bare Si, and sample B has a 2 nm layer of $SiO_2$ on top of Si. FIG. 11 illustrates the difference between $R_s$ of the two samples, the difference between $R_p$ of the two samples, and the difference between their phase-compensated spectra (e.g., as given by equation 8c). For this example, compensator 68 is an $MgF_2$ plate of thickness D=0.25 mm, and angle of incidence $\theta_i$ is 65°. From the figure, it is apparent that the phase-compensated and sensitivity-enhanced spectrum signal or PCSES is much more sensitive to the difference between the samples than $R_s$ or $R_p$. In particular, the $R_s$ and $R_p$ signals only differ significantly for wavelengths less than 400 nm, while the PCSES signal shows sensitivity over the entire wavelength range of the figure. Furthermore, the PCSES signal is desirably less sensitive to intensity fluctuations in source 52 and tilt of sample 72, because such changes have a relatively small effect on the phase term that PCSES is mainly responsive to, namely the $\delta$-dependent term in equations 8 and 9.

Figure 12:
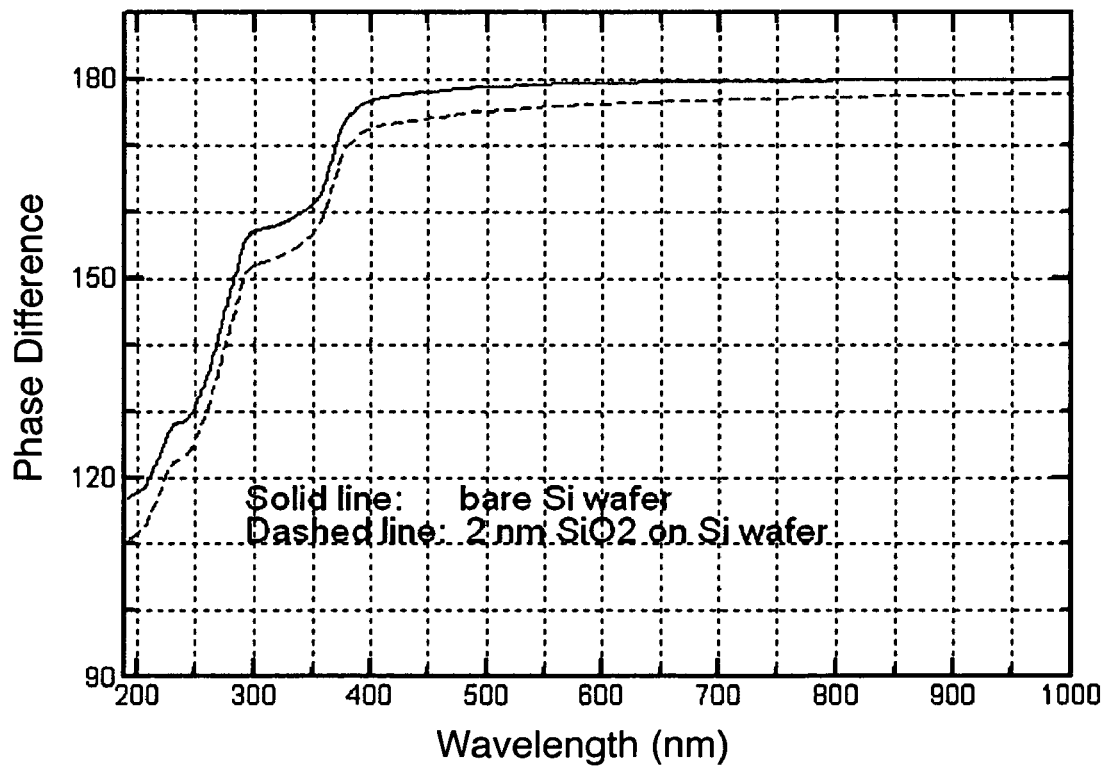
FIG. 12 is a plot of phase difference vs. wavelength for two different sample configurations.

The extended wavelength range of PCSES signal sample sensitivity as compared to $R_s$ and $R_p$ can be better appreciated in connection with FIG. 12, which shows $\delta(\lambda)$ for samples A and B of FIG. 11. Here it is apparent that the two samples have a noticeably different phase shift for all wavelengths, despite the fact that $R_s$ and $R_p$ for these two samples is virtually identically for wavelengths above 400 nm.

In the preceding examples, PCSES signals are oscillatory functions of wavelength. The reason for this is that in these examples compensators 26A, 26B, 68 or other supplementary compensators (not shown) are simple wave plates, e.g., an $MgF_2$ plate of thickness D=0.25 mm. Such plates have a retardance that depends significantly on wavelength (see discussion of $\lambda$ dependence of delimited phase shift $\Delta$). In particular, the retardance can vary by 720° or more (i.e., two or more 360° or $2\pi$ cycles) over spectral range 16 of source 12 or over the bandwidth spanned by discrete wavelengths $\lambda_1, \lambda_2, \lambda_3, \ldots \lambda_k$ emitted by source 52 in its non-continuous spectral emission mode. Now, oftentimes this wavelength dependence of compensator retardance is not a problem, as long as it does not overwhelm the optical resolution capabilities of detector 36 or 84. The enhanced sensitivity apparent in FIG. 11 is not materially affected by the fact that the phase-compensated spectrum or PCSES signal is an oscillatory function of wavelength as opposed to a non-oscillatory function of wavelength. Present-day curve fitting techniques can be employed to characterize samples by matching models to measured PCSES results (i.e., such modeling does not require non-oscillatory behavior vs. wavelength).

However, an oscillatory PCSES signal shows enhanced sensitivity to changes in sample 28 or 72 at some but not all wavelengths. Therefore, in an alternative approach, we employ a compensator or retardance element whose retardance depends much less significantly on wavelength than is the case for a wave plate. More specifically, such a compensator should have a retardance that varies by 180° or less over the range of wavelengths $\lambda_1, \lambda_2, \lambda_3, \ldots \lambda_k$ or over spectral range 16. In examining thin films, such as 48 or 71A, 71B, an ideal compensator 26A or 68 would provide $\cos(\Delta+\delta) \approx 0$ over spectral range 16 or bandwidth defined by $\lambda_1, \lambda_2, \lambda_3, \ldots \lambda_k$, where $\delta$ is the Si phase shift, and $\Delta$ is the delimited phase shift.

FIGS. 13a-c show some approaches for controlling compensator retardance. FIG. 13a shows the basic zero-order wave plate configuration, where a first wave plate 100, and a second wave plate 102 have their crystal axes orthogonal or perpendicular to each other. The net retardance of such an arrangement is determined by the thickness difference $\Delta D$ of plates 100, 102. A reasonable approximation to the ideal retardance behavior is obtained with a quartz zero-order wave plate having $\Delta D$=7.5 μm, or a $MgF_2$ zero-order wave plate having $\Delta D$=7 μm.

A somewhat improved approximation to the ideal can be obtained by assembling two zero-order wave plates with their net "fast axes" crossed, as shown in FIG. 13b. Here plates 100, 102 form a first zero-order wave plate 104, and plates 106, 108 form a second zero-order wave plate 110. The net "fast axes" of the first and second zero-order wave plates 104, 110 are crossed (i.e., first zero-order wave plate 104 has its net "fast axis" horizontal and second zero-order wave plate 110 has its net "fast axis" vertical, or vice versa). A still better approximation to an ideal retardance can be obtained by combining a $MgF_2$ zero-order wave plate having $\Delta D$=32.4 μm with a $SiO_2$ zero-order wave plate having $\Delta D$=27.6 μm in the same manner.

Another approach for providing well-matched phase compensation employs Fresnel rhombs. As shown in FIG. 13c, a Fresnel rhomb 112 provides retardance due to total internal reflection at surface of the element. A beam 114 passing through rhomb 112 experiences two total internal reflections. Thus, rhomb 112 provides a retardance of about 60° that has only a weak dependence on wavelength; i.e., it is approximately achromatic varying within a ±10° range.

Based on the above teachings, a person skilled in the art will recognize that any variety of birefringent elements and reflective elements such as prisms can be employed in making suitable compensators. Indeed, compensators 26A, 26B, 68 and/or any supplementary compensators or compensators used in alternative embodiments can be birefringent or reflective, as dictated by the limitations at hand. Theoretically, the ideal retardance situation means that $\cos(\Delta+\delta)\approx 0$ at all wavelengths, which is equivalent to $\Delta+\delta=90°$ or $270°$. With a $60°$ retarder, it is possible to ensure that the deviation from this ideal condition is no more than $30°$. To see this, consider all possible values of $\Delta$ in distinct ranges. If $0°<\delta<60°$ or $180°<\delta<240°$, the deviation from ideality is no more than $30°$ if $\Delta=60°$. If $60°<\delta<120°$ or $240°<\delta<300°$, the deviation from ideality is no more than $30°$ if $\Delta=0°$. If $120°<\delta<180°$ or $300°<\delta<360°$, the deviation from ideality is no more than $30°$ if $\Delta=-60°$. Since the PCSES signal at $30°$ departure from ideality is about 86% of the ideal signal, this approach can also provide substantial PCSES sensitivity at all wavelengths of interest.

FIG. 14 shows the retardance of the two designs shown in FIGS. 13a-c compared to the ideal retardance for Si PCSES. FIG. 15 shows the PCSES difference provided by the retarder designs, as well as by the ideal retarder, for 2 nm of $SiO_2$ on Si as compared to bare Si. Practical retarder designs are capable of providing performance comparable to that provided by an ideal retarder in this case.

However, a perfectly aligned zero-order waveplate, in which the "fast axis" of the first wave plate and the "slow axis" of the second wave plate are aligned within 1 arc minute, is hard and expensive to make. An alternative way is to have two separate single plates, with a desirable thickness difference $\Delta D$ that creates a $90°$ phase shift, for example, 7 μm for $MgO_2$, one as compensator 26A and another as supplementary compensator 26B in the embodiment shown in FIGS. 3 and 4. In this case, the alignment between these two plates does not need to be perfect, since each plate can be fully characterized (thickness D and retardance) and the misalignment can be determined through simulations and curve fitting. An example is shown in FIG. 16a. Equation 4 is used for calculations, in which $D_1=0.157$ mm, $D_2=0.15$ mm, $P=45°$, $A=-45°$ and sample 28 has a $SiO_2$ thin film 48 of thickness t=2 nm on top of a Si substrate. The solid line is for the perfect alignment ($C_1=0°$, $C_2=90°$), and the dotted line is for an imperfect alignment ($C_1=-1°$, $C_2=91°$). Ripples are seen in the misaligned measurement, from which $C_1$ and $C_2$ can be determined by curve fitting. Furthermore, these misalignments do not affect measurement sensitivity, as shown in FIG. 16b. This figure is similar to FIG. 15, where the difference in the measured intensities are plotted between no thin film 48 or t=0 Å and t=2 nm of $SiO_2$ on top of the Si substrate. The solid line is from systems with ideally aligned compensators 26A, 26B and dotted line is for misaligned compensators 26A, 26B with $C_1=-1°$, $C_2=91°$. No significant difference is observed between these two lines.

In the preceding exemplary embodiments, we have demonstrated the sensitivity of phase-compensated spectroscopy signal or PCSES sensitivity to changes in the vertical structure of a sample. For example, we have studied the presence or absence of a 2 nm layer of $SiO_2$ on Si. PCSES method is also applicable to characterization of critical dimensions on samples, e.g., lateral feature dimensions in layers such as 71A and/or 71B.

FIG. 17 shows an example of a typical critical dimension (CD) characterization. Here an Si substrate 120 lies beneath a 1 nm oxide film 122. A gate feature 124 having a height of 20 nm and average width of 7 nm is disposed on oxide film 122. Feature 124 is one element of a gate grating having a pitch of 42 nm. Other elements of this grating are not shown for reasons of clarity. Two cases are considered. In case A, the sidewall angle of feature 124 is $90°$ (i.e., top CD 124a and the bottom CD 124b are both 7 nm), and in case B, the sidewall angle of feature 124 is $87°$ (i.e., top CD 124a is 6 nm and bottom CD 124b is 8 nm).

FIG. 18 shows the difference in $R_s$, $R_p$ and PCSES between these two cases. The angle of incidence $\theta_i$ in this example is $7°$. The PCSES is seen to be more sensitive to CD change at short wavelengths. This extra information at short wavelengths can be very helpful in characterizing sample CD.

The preceding description is by way of example as opposed to limitation, and practice of the invention includes a variety of alternative embodiments. For example, various types of scanning, compound, continuous and single-wavelength sources may be used to provide the requisite radiation. Further, although above embodiments use detectors in combination with analyzers, a polarization-dependent detector that does away with the analyzer can also be used. Furthermore, although response beams examined above only explicitly reviewed reflected beams, transmitted beams can be used just as well. In those cases sample transmittances t as opposed to reflectances r need to be considered. These may be expressed with the aid of Jones matrix $J_T$:

$$J_T = \begin{pmatrix} t_{pp} & t_{ps} \\ t_{sp} & t_{ss} \end{pmatrix}.$$

Any additional mathematical conventions required to track multiple internal reflections and transmissions can be included in a manner that will be well known to the skilled artisan.

Clearly, the apparatus and method of invention are highly scalable and other embodiments of the apparatus and method are possible. Therefore, the scope of the invention should be judged by the appended claims and their legal equivalents.

I claim:

1. A method for phase-compensated spectroscopy comprising:
   a) deriving a beam of radiation in a polarization state $PS_p$ from a source emitting at a plurality of wavelengths;
   b) placing in said beam a compensator capable of altering said polarization state $PS_p$ by applying a delimited phase shift $\Delta$ between two orthogonal polarization axes to restrict a finely-vibrating spectrum;
   c) disposing a sample in said beam after said compensator to generate a response beam;
   d) passing a polarization state $PS_a$ of said response beam to a detector to measure a spectrum of said response beam;
   e) collecting a first spectrum when said polarization states $PS_p$, $PS_a$ and said compensator are in a first polarization-altering configuration;
   f) collecting a second spectrum when said polarization states $PS_p$, $PS_a$ and said compensator are in a second polarization-altering configuration; and
   g) deriving a phase-compensated spectrum from said first spectrum and said second spectrum.

2. The method of claim 1, wherein said first polarization-altering configuration comprises alignment of said polarization states $PS_p$, $PS_a$ and a principal axis of said compensator.

3. The method of claim 1, wherein said second polarization-altering configuration comprises non-alignment of said polarization states $PS_p$, $PS_a$ and a principal axis of said compensator.

4. The method of claim 3, wherein said non-alignment comprises a rotation of said principal axis of said compensator by 45° with respect to said first polarization-altering configuration.

5. The method of claim 1, wherein polarization state $PS_p$ is produced by a polarizing mechanism set at a rotation angle P, said polarization state $PS_a$ is produced by an analyzer set at a rotation angle A, said compensator is set at a rotation angle $C_1$, and said method further comprises placing a supplementary compensator set at a rotation angle $C_2$ in said response beam before said analyzer, whereby said rotation angles P, A, $C_1$, $C_2$ define said polarization-altering configurations.

6. The method of claim 5, wherein said rotation angles P, A, $C_1$, $C_2$ are measured with respect to a plane of incidence PI containing said beam incident on said sample and said response beam generated by said sample.

7. The method of claim 6, wherein in said first and second polarization-altering configurations said rotation angles P, A, $C_1$ and $C_2$ are selected from the group consisting of 0°, 45°, 90°, −45° and integer multiples thereof.

8. The method of claim 6, wherein in said first polarization-altering configuration P=−A=C=45° and in said second polarization-altering configuration P=−A=45°, C=0°, whereby said first spectrum is:

$$R_s+R_p-2\sqrt{R_sR_p}\cos\delta;$$

said second spectrum is:

$$R_s+R_p-2\sqrt{R_sR_p}\cos(\Delta+\delta);$$

where $\delta$ is the phase difference between $r_p$ and $r_s$, $R_s=|r_s|^2$, $R_p=|r_p|^2$ and said delimited phase shift $\Delta$ results from an effective polarization-altering contribution of the combination of $C_1$ and $C_2$.

9. The method of claim 8, wherein said phase-compensated spectrum T derived from said first spectrum and said second spectrum comprises a ratio:

$$T = \frac{R_s + R_p - 2\sqrt{R_sR_p}\cos(\Delta + \delta)}{R_s + R_p - 2\sqrt{R_sR_p}\cos\delta}.$$

10. The method of claim 6, wherein in said first polarization-altering configuration P=45°, A=45°, C=0° and said second polarization-altering configuration P=45°, A=45°, C=90°, whereby said first spectrum is:

$$T=\tfrac{1}{4}[R_s+R_p+2\sqrt{R_sR_p}\cos(\Delta+\delta)];$$

and said second spectrum is:

$$T=\tfrac{1}{4}[R_s+R_p+2\sqrt{R_sR_p}\cos(\Delta-\delta)];$$

where $\delta$ is the phase difference between $r_p$ and $r_s$, $R_s=|r_s|^2$, $R_p=|r_p|^2$ and said delimited phase shift $\Delta$ results from an effective polarization-altering contribution of the combination of $C_1$ and $C_2$.

11. The method of claim 6, wherein in said first polarization-altering configuration P=45°, A=−45°, C=0° and said second polarization-altering configuration P=45°, A=−45°, C=90°, whereby said first spectrum is:

$$T=\tfrac{1}{4}[R_s+R_p-2\sqrt{R_sR_p}\cos(\Delta+\delta)];$$

and said second spectrum is:

$$T=\tfrac{1}{4}[R_s+R_p-2\sqrt{R_sR_p}\cos(\Delta-\delta)];$$

where $\delta$ is the phase difference between $r_p$ and $r_s$, $R_s=|r_s|^2$, $R_p=|r_p|^2$ and said delimited phase shift $\Delta$ results from an effective polarization-altering contribution of the combination of $C_1$ and $C_2$.

12. The method of claim 1, wherein said delimited phase shift $\Delta$ of said compensator introduces a finely-vibrating spectrum that is adjusted to a spectral bandwidth SBW of said detector such that:

$$\frac{d\Delta}{d\lambda}\cdot SBW \ll \pi.$$

13. The method of claim 1, further comprising:
a) collecting a third spectrum when said polarization states $PS_p$, $PS_a$ and said compensator are in a third polarization-altering configuration; and
b) deriving said phase-compensated spectrum from said first spectrum, said second spectrum and said third spectrum.

14. The method of claim 13, further comprising:
a) collecting at least one supplementary spectrum when said polarization states $PS_p$, $PS_a$ and said compensator are in at least one corresponding polarization-altering configuration;
b) deriving said phase-compensated spectrum from said first spectrum, said second spectrum, said third spectrum and said at least one supplementary spectrum.

15. The method of claim 14, further comprising combining said first spectrum, said second spectrum, said third spectrum and said at least one supplementary spectrum to derive an ellipsometric measurement of said sample.

16. The method of claim 1, wherein said plurality of wavelengths span a continuous spectral range from VUV to IR.

17. The method of claim 1, wherein said sample is disposed such that an angle of incidence $\theta_i$ of said beam is in a range from 7° to 75°.

18. The method of claim 1, wherein said source emits unpolarized radiation at said plurality of wavelengths.

19. The method of claim 1, wherein a reference-sample is disposed in said beam of radiation for performing a calibration measurement.

20. An apparatus for phase-compensated spectroscopy comprising:
a) a source emitting at a plurality of wavelengths for deriving a beam of radiation in a polarization state $PS_p$;
b) a compensator placed in said beam for altering said polarization state $PS_p$ by applying a delimited phase shift $\Delta$ between two orthogonal polarization axes to restrict a finely-vibrating spectrum;
c) a sample disposed in said beam after said compensator to generate a response beam;
d) an analyzer for passing a polarization state $PS_a$ of said response beam;
e) a detector disposed in said response beam after said analyzer for measuring a spectrum of said response beam; and
f) a computing unit for collecting a first spectrum when said polarization states $PS_p$, $PS_a$ and said compensator are in a first polarization-altering configuration, collecting a second spectrum when said polarization states $PS_p$, $PS_a$ and said compensator are in a second polarization-altering configuration, and deriving a phase-compensated spectrum from said first spectrum and said second spectrum.

21. The apparatus of claim 20, wherein said source comprises a polarizing mechanism set at a rotation angle P for enforcing said polarization state $PS_p$, said compensator is set at a rotation angle $C_1$, and said apparatus further comprises:

a) an analyzer set at a rotation angle A for enforcing said polarization state $PS_a$;

b) a supplementary compensator disposed in said response beam before said analyzer and set at a rotation angle $C_2$; whereby said rotation angles P, A, $C_1$, $C_2$ define said polarization-altering configurations.

22. The apparatus of claim 21, wherein said rotation angles P, A, $C_1$, $C_2$ are defined with respect to a plane of incidence PI containing said beam incident on said sample and said response beam generated by said sample.

23. The apparatus of claim 21, wherein said polarizing mechanism comprises a polarizer.

24. The apparatus of claim 20, wherein said compensator is selected from the group of devices consisting of single wave plates, multiple wave plates, prisms, retarders, Berek plates and Fresnel rhombs.

25. The apparatus of claim 24, wherein said compensator is a multiple order wave plate having a thickness D ranging from 0.1 to 0.5 mm.

26. The apparatus of claim 24, wherein said compensator comprises at least one material selected from the group consisting of $MgF_2$ and $SiO_2$.

27. The apparatus of claim 24, wherein said compensator is an effective zero order retarder comprising a first multiple order wave plate before said sample and a second multiple order wave plate after said sample, said first multiple order wave plate and said second multiple order wave plate having their principal axes orthogonal to each other to substantially cancel said delimited phase shift Δ thereby achieving a zero order shift.

28. The apparatus of claim 24, wherein said compensator comprises a zero order wave plate and said delimited phase shift Δ extends from 0° to 360°.

29. The apparatus of claim 20, wherein said plurality of wavelengths spans a continuous spectral range from VUV to IR.

30. The apparatus of claim 20, wherein said sample is disposed such that an angle of incidence $\theta_i$ of said beam is in a range from 7° to 75°.

31. The apparatus of claim 20, further comprising an off-axis parabolic mirror for collimating at least one of said beam and said response beam.

32. The apparatus of claim 31, further comprising a toroidal reflector for imaging said source to an aperture.

33. The apparatus of claim 20, wherein said source is an unpolarized radiation source.

* * * * *